(12) United States Patent
Inoue et al.

(10) Patent No.: US 8,541,574 B2
(45) Date of Patent: Sep. 24, 2013

(54) ORGANOMETALLIC COMPLEX, AND LIGHT-EMITTING ELEMENT, LIGHT-EMITTING DEVICE AND ELECTRONIC DEVICE USING THE ORGANOMETALLIC COMPLEX

(71) Applicant: Semiconductor Energy Laboratory Co., Ltd., Kanagawa-ken (JP)

(72) Inventors: Hideko Inoue, Kanagawa (JP); Satoshi Seo, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 13/680,705

(22) Filed: Nov. 19, 2012

(65) Prior Publication Data

US 2013/0079516 A1    Mar. 28, 2013

Related U.S. Application Data

(62) Division of application No. 12/132,143, filed on Jun. 3, 2008, now abandoned.

(30) Foreign Application Priority Data

Jun. 4, 2007   (JP) ................................ 2007-148458

(51) Int. Cl.
    *C07F 15/00*    (2006.01)
(52) U.S. Cl.
    USPC ......................................................... 544/225
(58) Field of Classification Search
    USPC .......................................................... 544/225
    See application file for complete search history.

(56) References Cited

U.S. PATENT DOCUMENTS

| | | | |
|---|---|---|---|
| 6,821,646 | B2 | 11/2004 | Tsuboyama et al. |
| 7,220,495 | B2 | 5/2007 | Tsuboyama et al. |
| 2005/0221123 | A1 | 10/2005 | Inoue et al. |
| 2007/0129545 | A1 | 6/2007 | Inoue et al. |
| 2007/0241667 | A1 | 10/2007 | Ohsawa et al. |

FOREIGN PATENT DOCUMENTS

| | | |
|---|---|---|
| EP | 1 191 612 A2 | 3/2002 |
| JP | 2003-81988 | 3/2003 |
| JP | 2005-314414 | 11/2005 |
| JP | 2006-73992 | 3/2006 |
| JP | 2007-182429 | 7/2007 |
| WO | WO 2005/115061 A1 | 12/2005 |
| WO | WO 2007/066556 A1 | 6/2007 |

OTHER PUBLICATIONS

Tao, X.T. et al, "Metal Complex Polymer for Second Harmonic Generation and Electroluminescence Applications," Appl. Phys. Lett., vol. 70, No. 12, Mar. 24, 1997, pp. 1503-1505.
Inoue, H. et al, "6.1.4, Quencher and Photosensitizer," Basic Chemistry Course Photochemistry I, Maruzen Co., Ltd., publisher, Sep. 30, 1999, pp. 106-110 (with English abstract).
Salzer, A., "Nomenclature of Organometallic Compounds of the Transition Elements," IUPAC: International Union of Pure and Applied Chemistry, Pure Appl. Chem., vol. 71, No. 8, 1999, pp. 1557-1585.
Zhang, G-L et al, "Synthesis and Luminescence Property of a New Yellow Phosphorescent Iridium(III) Pyrazine Complex," Chemical Journal of Chinese Universities, vol. 25, No. 3, Mar. 2004, pp. 397-400 (with English abstract and full English translation).
International Search Report re application No. PCT/JP2006/323882, dated Jan. 16, 2007.
Written Opinion re application No. PCT/JP2006/323882, dated Jan. 16, 2007.

*Primary Examiner* — Brian McDowell
(74) *Attorney, Agent, or Firm* — Husch Blackwell LLP

(57) ABSTRACT

According to the present invention, a wider variation of organometallic complexes that can emit phosphorescence can be provided by applying, as a ligand, an organic compound from which a variety of derivatives can be easily synthesized. In particular, an organometallic complex having a sharp emission spectrum is provided. Further, an organometallic complex having high emission efficiency is provided. An organometallic complex represented by the general formula (G1) is provided. In the formula, Ar represents an aryl group, R represents an alkoxy group having 1 to 4 carbon atoms, and $R^1$ and $R^2$ individually represent either hydrogen or an alkyl group having 1 to 4 carbon atoms.

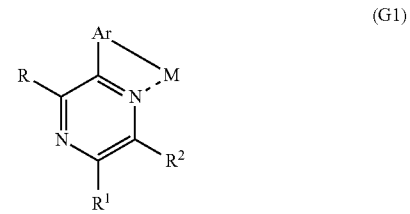

(G1)

3 Claims, 16 Drawing Sheets

ORGANOMETALLIC COMPLEX, AND LIGHT-EMITTING ELEMENT, LIGHT-EMITTING DEVICE AND ELECTRONIC DEVICE USING THE ORGANOMETALLIC COMPLEX

This application is a divisional of copending U.S. application Ser. No. 12/132,143, filed on Jun. 3, 2008.

TECHNICAL FIELD

The present invention relates to an organometallic complex. In particular, the present invention relates to an organometallic complex that is capable of converting a triplet excited state into luminescence. In addition, the present invention relates to a light-emitting element, a light-emitting device and an electronic device which use the organometallic complex.

BACKGROUND ART

Organic compounds absorb light, and thereby the compounds are converted to be in an excited state. By going through this excited state, such organic compounds generate various reactions (such as photochemical reactions) in some cases, or luminescence is produced in some cases. Therefore, various applications of the organic compounds have been being made.

As one example of the photochemical reactions, a reaction (oxygen addition) of singlet oxygen with an unsaturated organic molecule is known (refer to Reference 1: Haruo INOUE, et al., Basic Chemistry Course PHOTOCHEMISTRY I (Maruzen Co., Ltd.), pp. 106-110, for example). Since the ground state of an oxygen molecule is a triplet state, oxygen in a singlet state (singlet oxygen) is not generated by direct photoexcitation. However, singlet oxygen is generated in the presence of any other triplet excited molecule, which leads to an oxygen addition reaction. In this case, a compound capable of forming the triplet excited molecule is referred to as a photosensitizer.

As described above, in order to generate singlet oxygen, a photosensitizer that is capable of forming a triplet excited molecule by photoexcitation is necessary. However, since the ground state of an ordinary organic compound is a singlet state, photoexcitation to a triplet excited state is a forbidden transition, and a triplet excited molecule is hardly generated. Therefore, as such a photosensitizer, a compound which easily generates intersystem crossing from the singlet excited state to the triplet excited state (or a compound which allows the forbidden transition of photoexcitation directly to the triplet excited state) is required. In other words, such a compound can be used as a photosensitizer and is useful.

Also, such a compound often emits phosphorescence. The phosphorescence is luminescence generated by transition between different energies in multiplicity and in the case of an ordinary organic compound, indicates luminescence generated in returning from the triplet excited state to the singlet ground state (in contrast, luminescence in returning from a singlet excited state to a singlet ground state is referred to as fluorescence). Application fields of a compound capable of emitting phosphorescence, that is, a compound capable of converting a triplet excited state into luminescence (hereinafter, referred to as a phosphorescent compound), include a light-emitting element using an organic compound as a light-emitting substance.

This light-emitting element has a simple structure in which a light-emitting layer containing an organic compound that is a light-emitting substance is provided between electrodes, and has attracted attention as a next-generation flat panel display element because of its characteristics such as a thin shape, lightweight, high response speed, and low direct current voltage driving. In addition, a display device using this light-emitting element is superior in contrast, image quality, and wide viewing angle.

The emission mechanism of a light-emitting element in which an organic compound is used as a light-emitting substance is a carrier injection type. That is, by applying voltage with a light-emitting layer interposed between electrodes, electrons and holes injected from the electrodes are recombined to make the light-emitting substance excited, and light is emitted when the excited state returns to the ground state. As in the case of photoexcitation described above, types of the excited state include a singlet excited state (S*) and a triplet excited state (T*). Further, the statistical generation ratio thereof in a light-emitting element is considered to be S*:T*=1:3.

At room temperature, as for a compound capable of converting a singlet excited state to luminescence (hereinafter, referred to as a fluorescent compound), only luminescence from the singlet excited state (fluorescence) is observed, but luminescence from the triplet excited state (phosphorescence) is not observed. Therefore, in a light-emitting element using a fluorescent compound, the theoretical limit of internal quantum efficiency (the ratio of generated photons to injected carriers) is considered to be 25% based on S*:T*=1:3.

On the other hand, when the phosphorescent compound described above is used, the internal quantum efficiency can be improved to 75 to 100% in theory. Namely, a light emission efficiency that is 3 to 4 times as much as that of the fluorescence compound can be achieved. For these reasons, in order to achieve a highly-efficient light-emitting element, a light-emitting element using a phosphorescent compound has been developed actively (for example, refer to Reference 2: Zhang, Guo-Lin, et al., Gaodeng Xuexiao Huaxue Xuebao (2004), vol. 25, No. 3, pp. 397-400). In particular, as the phosphorescent compound, an organometallic complex using iridium or the like as a central metal has been attracting attention, owing to its high phosphorescence quantum yield.

DISCLOSURE OF THE INVENTION

The organometallic complex disclosed in Reference 2 can be expected to be used as a photosensitizer, since it easily causes intersystem crossing. In addition, since the organometallic complex easily generates luminescence (phosphorescence) from a triplet excited state, a highly efficient light-emitting element is expected by using the organometallic complex for the light-emitting element. However, in the present state, the number of types of such organometallic complexes is small.

For example, a pyrazine derivative which is used as a ligand of the organometallic complex disclosed in Reference 2 is synthesized by a dehydration condensation reaction of ethylenediamine and β-diketone (benzyl) and a dehydrogenation reaction following the dehydration condensation reaction; however, there are limitations on the types of ethylenediamine derivatives and β-diketone which can be used as raw materials, and thus, the types of pyrazine derivatives are also limited. Therefore, naturally, there are also limitations on the types of organometallic complexes using the pyrazine derivative as a ligand.

Further, the organometallic complex disclosed in Reference 2 has a problem in that the emission spectrum is broad. This lowers the color purity and thus is disadvantageous for application to full color display devices in teens of color reproductively. This organometallic complex emits red-orange color light; however, if the emission spectrum is broad, the spectrum extends to a region of deep red to infrared, which leads to lower emission efficiency (visibility efficiency (cd/A)).

As described above, it is an object of the present invention to provide a wider variation of organometallic complexes that can emit phosphorescence by applying, as a ligand, an organic compound from which a variety of derivatives can be easily synthesized. In particular, it is another object of the present invention to provide an organometallic complex by which a light-emitting element having a sharp emission spectrum can be formed. Further, it is another object of the present invention to provide an organometallic complex having high emission efficiency.

Moreover, it is another object of the present invention to provide a light-emitting element with wide variations of light emission of green to red colors by manufacturing a light-emitting element using such an organometallic complex. It is still another object of the present invention to provide a light-emitting element with high color purity. It is still another object of the present invention to provide a light-emitting element having high light-emitting efficiency. It is still another object to provide a light-emitting device and an electronic device with reduced power consumption.

The present inventors have made researches keenly. As a result, the present inventors have invented that a pyrazine derivative represented by the following general formula (G0) is ortho-metalated with a metal ion of Group 9 or Group 10 in the periodic table, and thereby an organometallic complex can be obtained, the organometallic complex can easily cause intersystem crossing, and emit phosphorescence. Further, the present inventors have found that emission spectrum of a light-emitting element formed using an organometallic complex having the structure of the general formula (G0) which is ortho-metalated is especially sharp.

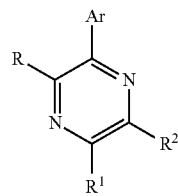

(G0)

In the formula, Ar represents an aryl group, R represents an alkoxy group having 1 to 4 carbon atoms, $R^1$ and $R^2$ individually represent either hydrogen or an alkyl group having 1 to 4 carbon atoms.

Therefore, a structure of the present invention is an organometallic complex including a structure represented by a general formula (G1).

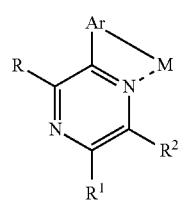

(G1)

In the formula, Ar represents an arylene group; R represents an alkoxy group having 1 to 4 carbon atoms; $R^1$ and R2 individually represent hydrogen or an alkyl group having 1 to 4 carbon atoms; and M is a central metal and represents an element belonging to Group 9 or Group 10 in the periodic table.

In addition, when $R^2$ in the above general formula (G0) is hydrogen, the pyrazine derivative represented by the general formula (G0) is easy to be ortho-metalated with a metal ion, since steric hindrance is small, which is preferable in terms of yield in synthesis. Accordingly, a preferred structure of the present invention is an organometallic complex including a structure represented by the following general formula (G2).

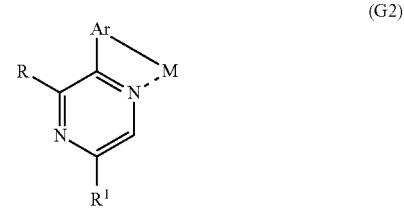

(G2)

In the formula, Ar represents an arylene group; R represents an alkoxy group having 1 to 4 carbon atoms; $R^1$ represents hydrogen or an alkyl group having 1 to 4 carbon atoms; and M is a central metal and represents an element belonging to Group 9 or Group 10 in the periodic table.

Preferably, $R^2$ and $R^1$ in the above general formula (G0) are hydrogen and an alkyl group, respectively, in tennis of yield in synthesis of the organometallic complex. Accordingly, a preferred structure of the present invention is an organometallic complex including a structure represented by the following general formula (G2).

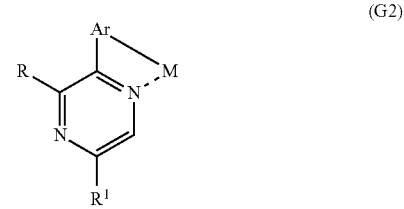

(G2)

In the formula, Ar represents an arylene group; R represents an alkoxy group having 1 to 4 carbon atoms; $R^1$ represents an alkyl group having 1 to 4 carbon atoms; and M is a central metal and represents an element belonging to Group 9 or Group 10 in the periodic table.

In addition, in the organometallic complex having the structure represented by the above general formula (G2), a phenylene group is preferable for the arylene group (Ar). By introducing a substituent to the phenylene group, emission color with wide region of green color to red color can be realized. Accordingly, a preferred structure of the present invention is an organometallic complex including a structure represented by the following general formula (G3).

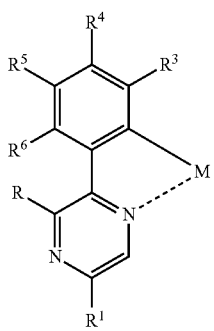

(G3)

In the formula, R represents an alkoxy group having 1 to 4 carbon atoms; $R^1$ represents an alkyl group having 1 to 4 carbon atoms; $R^3$ to $R^6$ individually represent hydrogen, an alkyl group, an alkoxy group, a halogen group, a haloalkyl group, an aryl group, a dialkylamino group, or a diarylamino group; M is a central metal and represents an element belonging to Group 9 or Group 10 in the periodic table.

In addition, in the organometallic complex having the structure represented by the above general formula (G2), conjugation of the arylene group (Ar) is expanded to obtain red emission color, which is useful. Accordingly, another preferred structure of the present invention is an organometallic complex including a structure represented by the following general formula (G4).

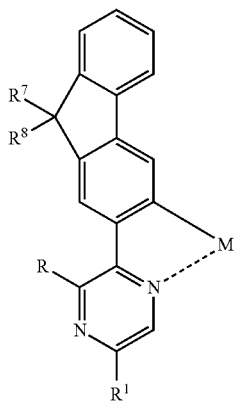

(G4)

In the formula, R represents an alkoxy group having 1 to 4 carbon atoms; $R^1$ represents an alkyl group having 1 to 4 carbon atoms; $R^7$ and $R^8$ represent an alkyl group having 1 to 4 carbon atoms; and M is a central metal and represents an element belonging to Group 9 or Group 10 in the periodic table.

In addition, in the organometallic complex having the structure represented by the above general formula (G3), specifically, an organometallic complex having a structure represented by the following general formula (G5) is preferable in terms of yield in synthesis.

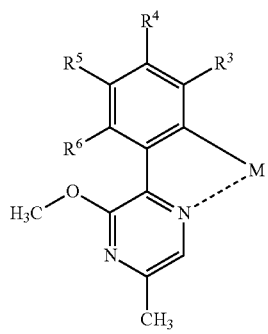

(G5)

In the formula, $R^3$ to $R^6$ individually represent hydrogen, an alkyl group, an alkoxy group, a halogen group, a haloalkyl group, an aryl group, a dialkylamino group, or a diarylamino group; M is a central metal and represents an element belonging to Group 9 or Group 10 in the periodic table.

In addition, in the organometallic complex having the structure represented by the above general formula (G4), specifically, an organometallic complex having a structure represented by the following general formula (G6) is preferable in terms of yield in synthesis.

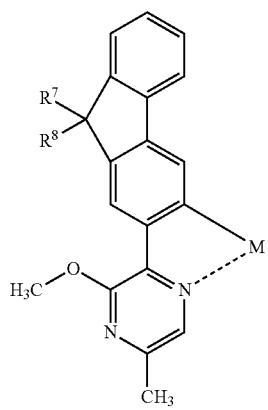

(G6)

In the formula, $R^7$ and $R^8$ represent an alkyl group having 1 to 4 carbon atoms; and M is a central metal and represents an element belonging to Group 9 or Group 10 in the periodic table.

Here, as the organometallic complex having the structure represented by the general formula (G1), more specifically, an organometallic complex represented by the following general formula (G7) is preferable since it can be easily synthesized.

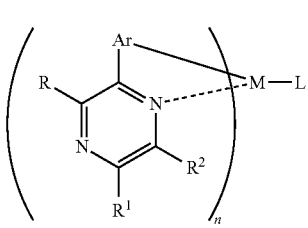

(G7)

In the formula, Ar represents an arylene group; R represents an alkoxy group having 1 to 4 carbon atoms; $R^1$ and $R^2$ individually represent hydrogen or an alkyl group having 1 to 4 carbon atoms; M is a central metal and represents an element belonging to Group 9 or Group 10 in the periodic table; L represents a monoanionic ligand; and n is 2 when the M is an element belonging to Group 9, and n is 1 when the M is an element belonging to Group 10.

As the organometallic complex having the structure represented by the above general formula (G2), an organometallic complex represented by the following general formula (G8) is specifically preferable because it can be easily synthesized.

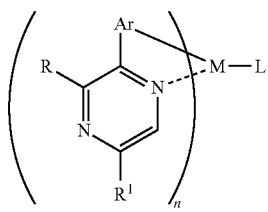

(G8)

In the formula, Ar represents an arylene group; R represents an alkoxy group having 1 to 4 carbon atoms; $R^1$ represents hydrogen or an alkyl group having 1 to 4 carbon atoms; M is a central metal and represents an element belonging to Group 9 or Group 10 in the periodic table; L represents a monoanionic ligand; and n is 2 when the M is an element belonging to Group 9, and n is 1 when the M is an element belonging to Group 10.

In addition, in the above general formula (G7), preferably, $R^2$ and $R^1$ are hydrogen and an alkyl group, respectively, in terms of yield in synthesis of the organometallic complex. Therefore, a preferred structure of the present invention is an organometallic complex represented by the following general formula (G8).

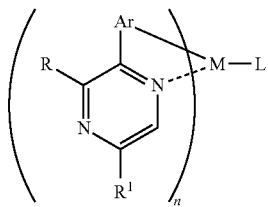

(G8)

In the formula, Ar represents an arylene group; R represents an alkoxy group having 1 to 4 carbon atoms; $R^1$ represents an alkyl group having 1 to 4 carbon atoms; M is a central metal and represents an element belonging to Group 9 or Group 10 in the periodic table; L represents a monoanionic ligand; and n is 2 when the M is an element belonging to Group 9, and n is 1 when the M is an element belonging to Group 10.

In addition, in the organometallic complex represented by the above general formula (G8), a phenylene group is preferable for the arylene group (Ar). By introducing a substituent to the phenylene group, emission color with wide region of green color to red color can be realized. Accordingly, a preferred structure of the present invention is an organometallic complex represented by the following general formula (G9).

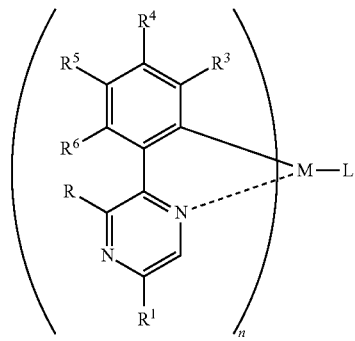

(G9)

In the formula, R represents an alkoxy group having 1 to 4 carbon atoms; $R^1$ represents an alkyl group having 1 to 4 carbon atoms; $R^3$ to $R^6$ individually represent hydrogen, an alkyl group, an alkoxy group, a halogen group, a haloalkyl group, an aryl group, a dialkylamino group, or a diarylamino group; M is a central metal and represents an element belonging to Group 9 or Group 10 in the periodic table; L represents a monoanionic ligand; and n is 2 when the M is an element belonging to Group 9, and n is 1 when the M is an element belonging to Group 10.

Note that, in the organometallic complex represented by the above general formula (G8), conjugation of the arylene group (Ar) is expanded to obtain red emission color, which is useful. Accordingly, a preferred structure of the present invention is an organometallic complex including a structure represented by the following general formula (G10).

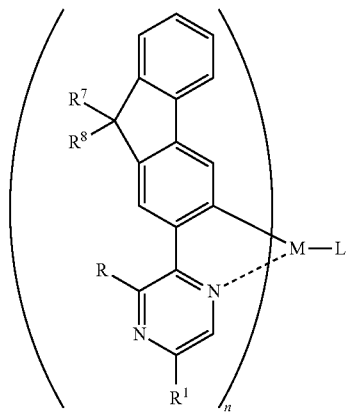

(G10)

In the formula, R represents an alkoxy group having 1 to 4 carbon atoms; $R^1$ represents an alkyl group having 1 to 4 carbon atoms; $R^7$ and $R^8$ represent an alkyl group; M is a central metal and represents an element belonging to Group 9 or Group 10 in the periodic table; L represents a monoanionic ligand; and n is 2 when the M is an element belonging to Group 9, and n is 1 when the M is an element belonging to Group 10.

As the organometallic complex having the structure represented by the above general formula (G9), an organometallic complex represented by the following general formula (G11) is specifically preferable in terms of yield in synthesis.

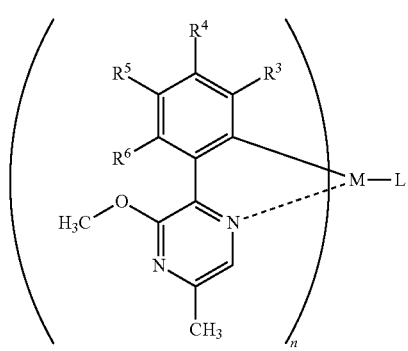
(G11)

In the formula, $R^3$ to $R^6$ individually represent hydrogen, an alkyl group, an alkoxy group, a halogen group, a haloalkyl group, an aryl group, a dialkylamino group, or a diarylamino group; M is a central metal and represents an element belonging to Group 9 or Group 10 in the periodic table; L represents a monoanionic ligand; and n is 2 when the M is an element belonging to Group 9, and n is 1 when the M is an element belonging to Group 10.

Further, as the organometallic complex represented by the above general formula (G10), more specifically, an organometallic complex represented by the following general formula (G12) is preferable in terms of yield in synthesis.

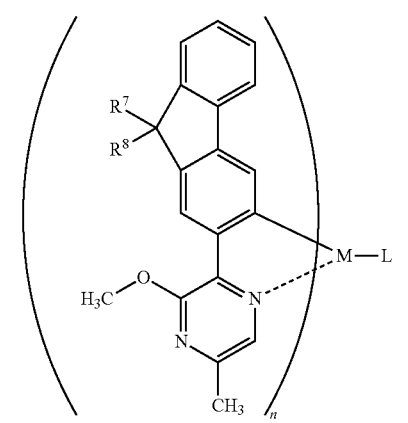
(G12)

In the formula, $R^7$ and $R^8$ represent an alkyl group having 1 to 4 carbon atoms; M is a central metal and represents an element belonging to Group 9 or Group 10 in the periodic table; L represents a monoanionic ligand; and n is 2 when the M is an element belonging to Group 9, and n is 1 when the M is an element belonging to Group 10.

The above-mentioned monoanionic ligand L is preferably either a monoanionic bidentate chelate ligand having a β-diketone structure, a monoanionic bidentate chelate ligand having a carboxyl group, a monoanionic bidentate chelate ligand having a phenolic hydroxyl group, or a monoanionic bidentate chelate ligand in which two ligand elements are both nitrogen. More preferably, the monoanionic ligand L is a monoanionic ligand represented by the following structural formulae (L1) to (L8). Since these ligands have high coordinative ability and can be obtained at low price, they are useful.

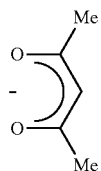
(L1)

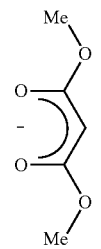
(L2)

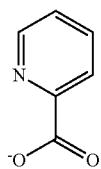
(L3)

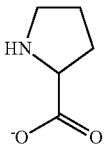
(L4)

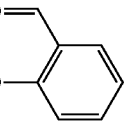
(L5)

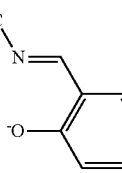
(L6)

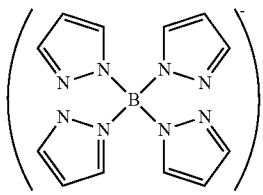
(L7)

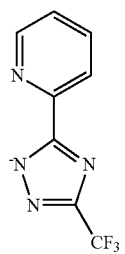
(L8)

For more efficient emission of phosphorescence, a heavy metal is preferable as a central metal in terms of a heavy atom effect. Therefore, one feature of the present invention is that iridium or platinum is employed as the central metal M in the above organometallic complexes of the present invention.

In the organometallic complexes having the structure represented by the above general formulae (G1) to (G6) (in other words, including the organometallic complexes represented by the above general formulae (G7) to (G12)), the coordinate structure in which the pyrazine derivative represented by the general formula (G0) is ortho-metalated with a metal ion, contributes emission of phosphorescence greatly. Thus, the above organometallic complexes can be preferably used as a light-emitting material. In addition, a light-emitting element formed using the organometallic complex has a sharp emission spectrum, and thus its color purity is excellent. Therefore, an organometallic complex of the present invention is effective as a light-emitting material. Therefore, another structure of the present invention is a light-emitting material including such an organometallic complex as described above.

In addition, the organometallic complex of the present invention can emit phosphorescence. In other words, a triplet excited energy can be converted into light, and thus high efficiency can be obtained by applying the organometallic complex to a light-emitting element. Thus, the organometallic complex of the present invention is very effective. In addition, by using an organometallic complex of the present invention for a light-emitting element, the light-emitting element can have a sharp emission spectrum and can light emission with high color purity. Therefore, the present invention also includes a light-emitting element using an organometallic complex of the present invention.

At this time, the organometallic complex of the present invention is effective when it is used for a light-emitting substance in terms of emission efficiency. Therefore, one feature of the present invention is a light-emitting element using the organometallic complex of the present invention as a light-emitting substance.

The thus obtained light-emitting element of the present invention can realize high light emission efficiency, and thus a light-emitting device (such as an image display device or a light-emitting device) using this light-emitting element can realize low power consumption. Further, since the light-emitting element has high color purity, a light-emitting device using the light-emitting element (e.g., an image display device or a light-emitting device) can provide high-quality image. Accordingly, the present invention includes a light-emitting device, an electronic device, and the like using the light-emitting element of the present invention.

In this specification, the term "light-emitting device" refers to an image display device or a light-emitting device including a light-emitting element. Further, the category of the light-emitting device includes a module including a light-emitting element attached with a connector such as a module attached with an anisotropic conductive film, TAB (Tape Automated Bonding) tape, or a TCP (Tape Carrier Package); a module in which the top of the TAB tape or the TCP is provided with a printed wiring board; or a module in which an IC (Integrated Circuit) is directly mounted on a light-emitting element by COG (Chip On Glass); and the like. Further, the category includes a light-emitting device used for an illumination apparatus and the like.

By carrying out the present invention, a wider variety of organometallic complexes that can emit phosphorescence, in particular, a wider variety of organometallic complexes, with which a light-emitting element having a sharp emission spectrum can be formed, can be provided. Moreover, an organometallic complex having high emission efficiency can be provided.

Further, by forming a light-emitting element using an organometallic complex of the present invention, a light-emitting element having high color purity can be provided. Further, a light-emitting element having a wider variation of emission color from green to red can be provided. Moreover, a light-emitting element having high emission efficiency can be provided.

By using organometallic complexes of the present invention, light-emitting devices and electronic devices that can provide high-quality images can be provided. Moreover, it is another object of the present invention to provide light-emitting devices and electronic devices with reduced power consumption.

BEST MODE FOR CARRYING OUT THE INVENTION

Embodiment Mode

Figure 1:
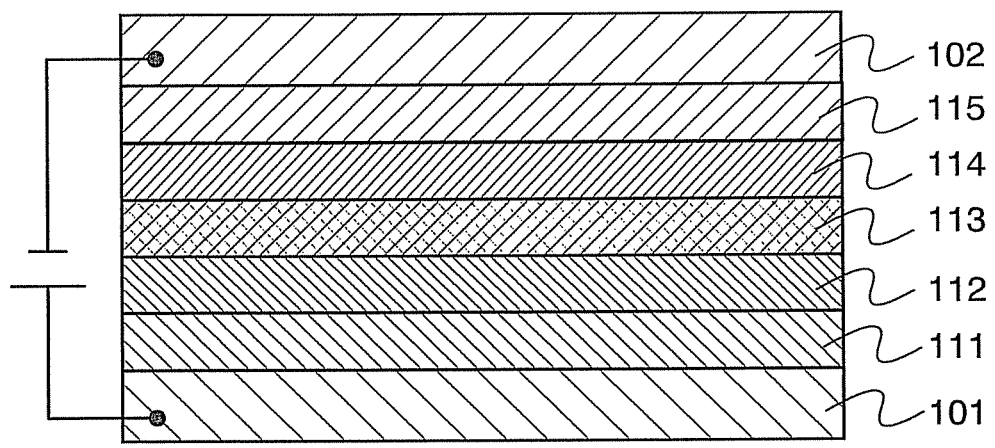
FIG. 1 illustrates a structure of a light-emitting element using an organometallic complex according to an aspect of the present invention.

Hereinafter, embodiment modes of the present invention will be described in detail with reference to the accompanying drawings. Note that the present invention is not limited to the following description, and it is easily understood by those skilled in the art that modes and details thereof can be modified in various ways without departing from the spirit and the scope of the invention. Therefore, it should be noted that the present invention should not be interpreted as being limited to the description of embodiment modes.

(Embodiment Mode 1)

Embodiment Mode 1 will describe an organometallic complex of the present invention.

<<Synthesis Method of an Alkoxypyrazine Derivative Represented by a General Formula (G0)>>

An organometallic complex of the present invention is faulted by ortho metalation of a 2-alkoxy-3-arylpyrazine derivative represented by the following general formula (G0) with respect to an ion of a metal belonging to Group 9 or Group 10.

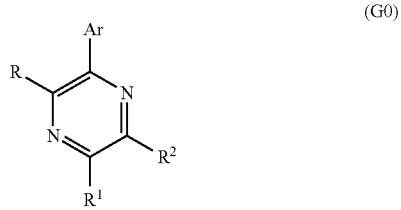

(G0)

In the formula, Ar represents an aryl group. R represents an alkoxy group having 1 to 4 carbon atoms, and R$^1$ and R$^2$ individually represent hydrogen or an alkyl group having 1 to 4 carbon atoms.

The 2-alkoxy-3-arylpyrazine derivative represented by the general formula (G0) can be synthesized by the following simple synthetic scheme. For example, as represented by the following scheme (a), the 2-alkoxy-3-arylpyrazine derivative can be obtained by reacting a chloropyrazine derivative (A1) with alkoxide (A2). Alternatively, as shown in the following scheme (a'), a halide of areae (A1') is lithiated with alkyllithium or the like, and is reacted with an alkoxypyrazine derivative (A2'), thereby obtaining the 2-alkoxy-3-arylpyrazine derivative. Alternatively, as shown in the following scheme (a''), 2-alkoxy-3-arylpyrazine (A1'') is reacted with lithiations (A2''-1) and (A2''-2) in R$^1$ nd R$^2$, whereby the 2-alkoxy-3-arylpyrazine derivative can be obtained. X in the formula denotes a halogen element.

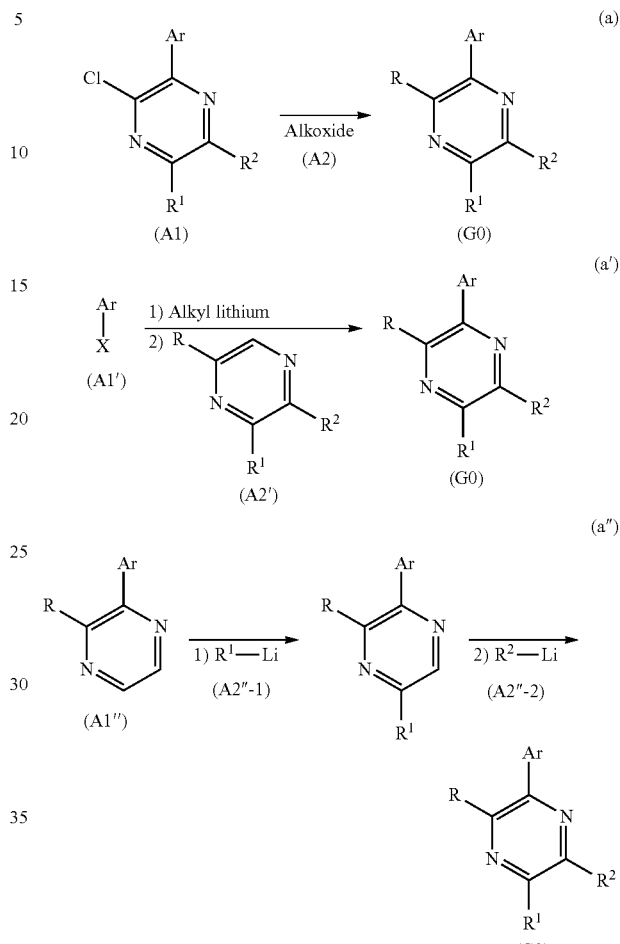

Since various kinds of the above-described compounds (A1), (A2), (A1'), (A2'), (A1''), (A2''-1), and (A2''-2) are available commercially or can be synthesized, many kinds of the alkoxypyrazine derivative represented by the above-described general formula (G0) can be synthesized. Accordingly, the organometallic complexes of the present invention have wider variations of ligands.

<<Synthesis Method of an Organometallic Compound of the Present Invention Having a Structure Represented by a General Formula (G1)>>

Next, an organometallic complex of the present invention which is formed by ortho metalation of the 2-alkoxy-3-arylpyrazine derivative represented by (G0), i.e., an organometallic complex having the structure represented by the following general formula (G1) will be described.

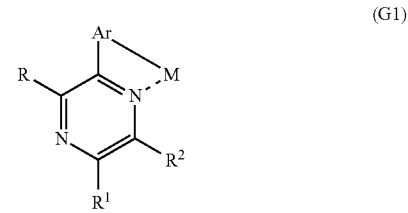

(G1)

In the formula, Ar represents an arylene group. R represent an alkoxy group having 1 to 4 carbon atoms. $R^1$ and $R^2$ individually represent hydrogen or an alkyl group having 1 to 4 carbon atoms. M is a central metal and represents either an element belonging to Group 9 or an element belonging to Group 10.

First, as represented by the following synthesis scheme (b), 2-alkoxy-3-arylpyrazine derivative represented by the general formula (G0) and a compound of metal belonging to Group 9 or Group 10 and including halogen (a metal halide or a metal complex) is heated with an alcohol solvent (such as glycerol, ethyleneglycol, 2-methoxyethanol, or 2-ethoxyethanol) alone or a mixed solvent of one kind or more of such alcohol solvents and water, so that a binuclear complex (B), which is a kind of organometallic complexes of the present invention having the structure represented by the general formula (G1), can be obtained. As a compound including a metal belonging to Group 9 or Group 10 and including halogen, there are given rhodium chloride hydrate, palladium chloride, iridium chloride hydrate, iridium chloride hydrochloride hydrate, potassium tetrachloroplatinate(II), and the like; however, the present invention is not limited to these examples. In the scheme (b), M denotes an element belonging to Group 9 or Group 10, and X denotes a halogen element. In addition, n is 2 when M is an element belonging to Group 9, and n is 1 when M is an element belonging to Group 10.

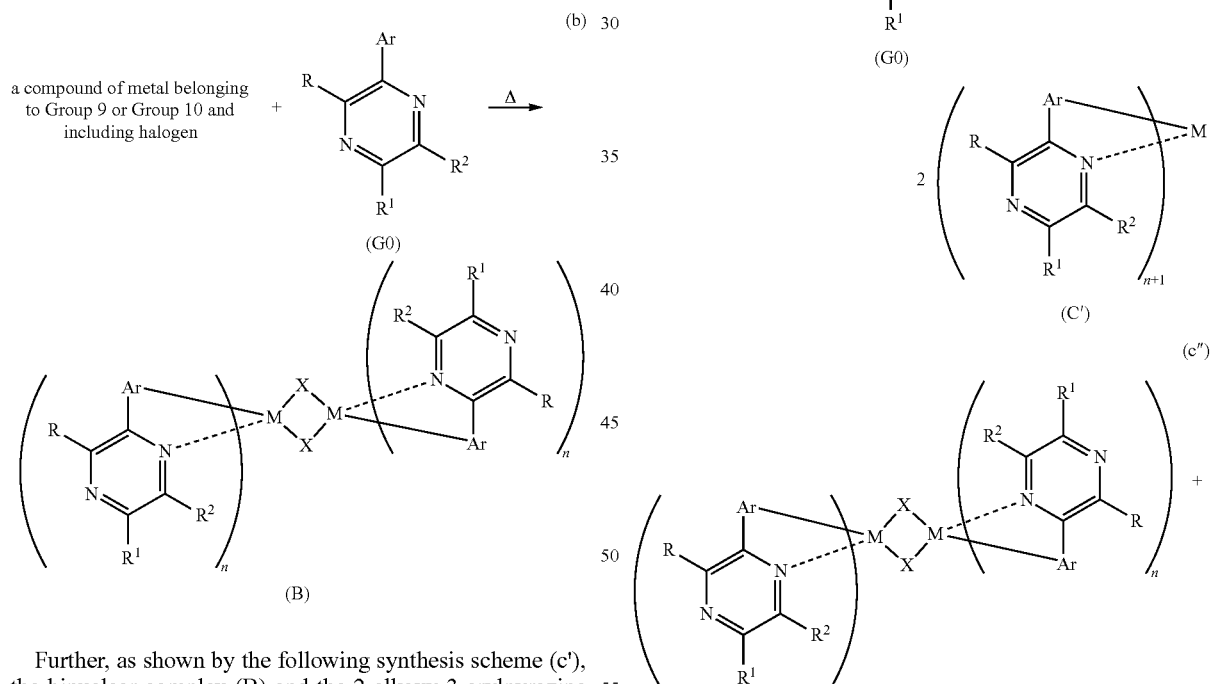

Further, as shown by the following synthesis scheme (c'), the binuclear complex (B) and the 2-alkoxy-3-arylpyrazine derivative represented by the general formula (G0) are heated at a high temperature of about 200° C. in a high boiling solvent of glycerol or the like, and thus one type (C') of organometallic complexs of the present invention including the structure represented by the general formula (G1) can be obtained. As shown in the synthesis scheme (c"), a binuclear complex (B) and a compound which can be ortho-metalated, such as phenylpyridine (more typically, a compound which can be cyclo-metalated) are heated at a high temperature of around 200° C. in a high boiling solvent of glycerol or the like, and thus, one type (C") of organometallic complexes of the present invention including the structure represented by the general formula (G1) can be obtained. In the schemes (c') and (c"), M denotes an element belonging to Group 9 or Group 10, and X denotes a halogen element. In addition, n is 2 when M is an element belonging to Group 9, and n is 1 when M is an element belonging to Group 10.

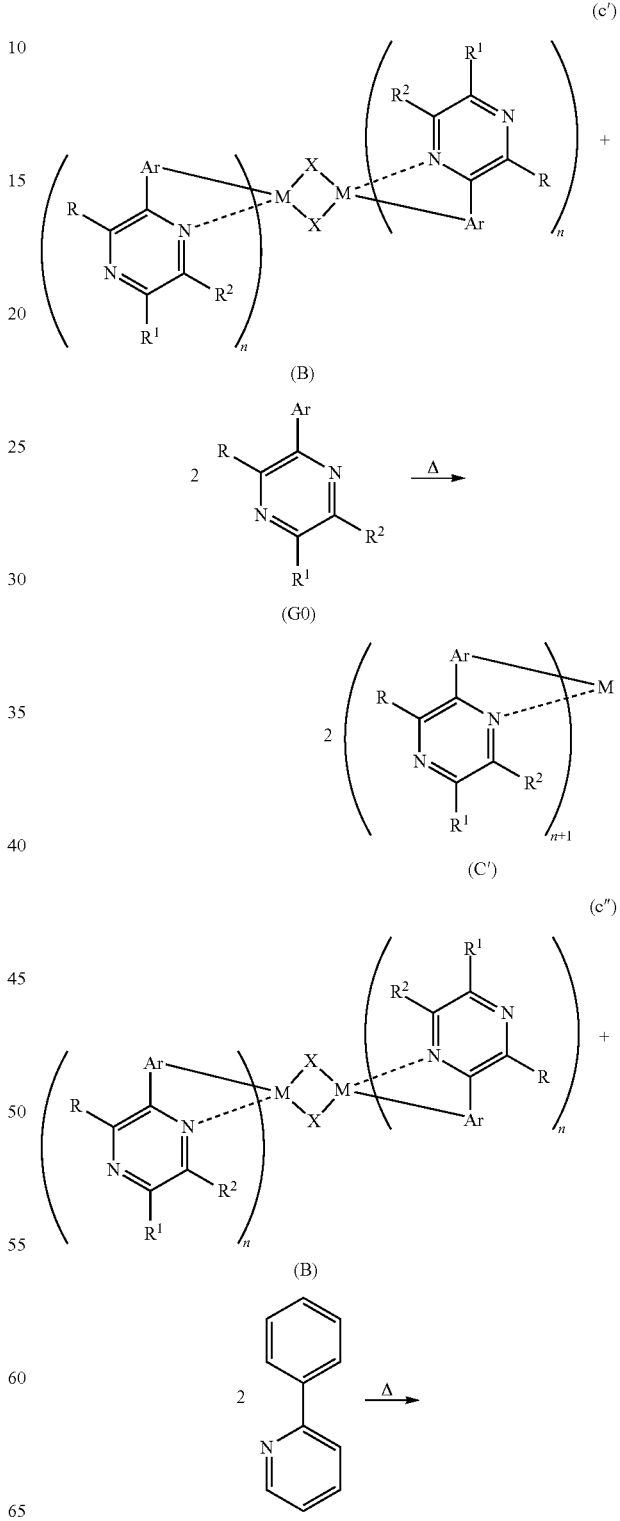

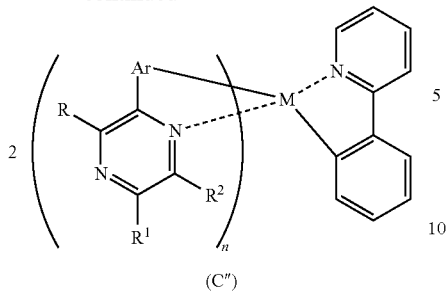

(C″)

<<A Synthesis Method of an Organometallic Complex Represented by a General Formula (G7)>

A preferable example, i.e., an organometallic complex represented by the general formula (G7), among organometallic complexes having the structure represented by the above general formula (G1), will be described.

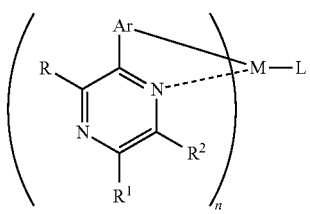

(G7)

In the formula, Ar represents an arylene group. R represents an alkoxy group having 1 to 4 carbon atoms. $R^1$ and $R^2$ individually represent either hydrogen or an alkyl group having 1 to 4 carbon atoms. M is a central metal and represents either an element belonging to Group 9 or an element belonging to Group 10. L represents a monoanionic ligand. In addition, n is 2 when M is an element belonging to Group 9, and n is 1 when M is an element belonging to Group 10.

The organometallic complex of the present invention represented by the above general formula (G7) can be synthesized by the following scheme (c). In other words, the binuclear complex (B) obtained by the above scheme (b) is reacted with a material HL of a monoanionic ligand, and a proton of HL is eliminated and coordinated to the central metal M. In this manner, the organometallic complex of the present invention represented by the general formula (G7) can be obtained. In the scheme (c), M denotes an element belonging to Group 9 or Group 10, and X denotes a halogen element. In addition, n is 2 when M is an element belonging to Group 9, and n is 1 when M is an element belonging to Group 10.

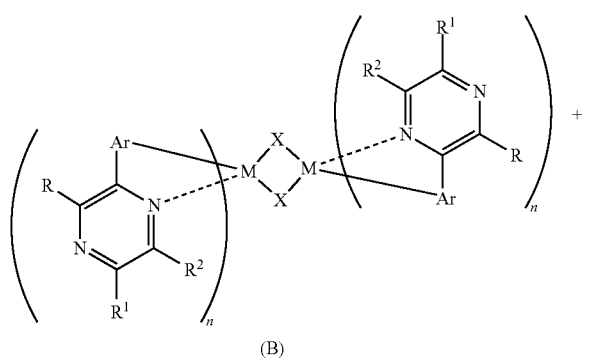

(B)

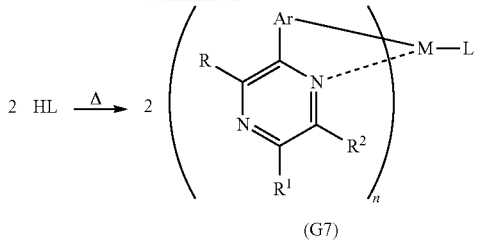

(G7)

<<An Organometallic Complex of the Present Invention Represented by the General Formula (G1), and a Specific Structural Formula of an Organometallic Complex of the Present Invention which is Represented by the General Formula (G7)>>

Then, specific structural formulae of the organometallic complex of the present invention having the structure shown by the general formula (G1), and the organometallic complex of the present invention represented by the general formula (G7) will be described.

The central metal M is selected from elements belonging to Group 9 or Group 10; however, iridium(III) or platinum(II) is preferable in terms of emission efficiency. In particular, iridium(III) is preferably used, since it is thermally stable.

In addition, as specific examples of R in the formula (G1) or (G7), an alkyl group such as a methyl group, an ethyl group, an isopropyl group, or an n-butyl group can be given. By adopting such a substituent to R, a synthesis yield of an organometallic complex can be more enhanced than when R is hydrogen. As compared with when a conjugated group (such as a phenyl group) is used for R, emission spectrum of a light-emitting element Mimed using the organometallic complex can be more sharpened, and thus color purity can be increased.

As specific examples of $R^1$ and $R^2$, an alkyl group typified by a methyl group, an ethyl group, an isopropyl group, an n-butyl group or the like can be used as well as hydrogen.

As specific examples of Ar, a phenylene group, a phenylene group in which at least one hydrogen is substituted by an alkyl group such as a methyl group, a phenylene group in which at least one hydrogen is substituted by an alkoxy group such as a methoxy group, a phenylene group in which at least one hydrogen is substituted by a hologen group such as a fluoro group, a phenylene group in which at least one hydrogen is substituted by a trifluoromethyl group, a phenylene group in which at least one hydrogen is substituted by a phenyl group, a phenylene group in which at least one hydrogen is substituted by a dialkylamino group such as a dimethylamino group, a phenylene group in which at least one hydrogen is substituted by a diarylamino group such as a diphenylamino group are given. In particular, by using a phenylene group in which at least one hydrogen is substituted by a halogen group or a trifluoromethyl group for Ar, emission wavelength can be shifted to a shorter wavelength than when an unsubstituted phenylene group is used for Ar. By using a phenylene group substituted by a dialkylamino group or a diarylamino group for Ar, emission wavelength can be shifted to a longer wavelength than when an unsubstituted phenylene group is used for Ar. Further, as Ar, 9,9-dimethylfluorene-diyl group such as 9,9-dialkylfluorene-diyl can be applied. In that case, emission wavelength can be shifted to a longer wavelength side than when Ar adopts an unsubstituted phenylene group.

Next, the monoanionic ligand L in the above general formula (G7) is described. The monoanionic ligand L is preferably any one of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen, because these ligands have high coordinating ability. More specifically, monoanionic ligands represented by the following structural formulae (L1) to (L8) are given. However, the monoanionic ligand L is not limited to these examples.

(L1)
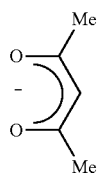

(L2)
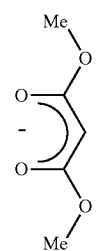

(L3)
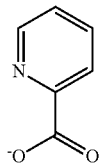

(L4)
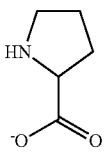

(L5)
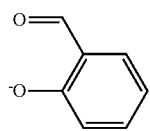

(L6)
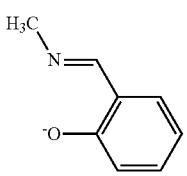

(L7)
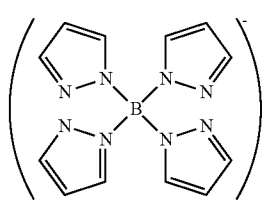

(L8)
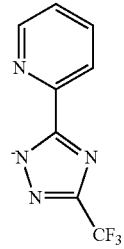

By using the central metal M, the substituents R, $R^1$ and Ar, the monoanionic ligand L as described above in combination as appropriate, an organometallic complex of the present invention is constituted. Hereinafter, specific structural formulae (1) to (47) of organometallic complexes of the present invention are given. Note that the present invention is not limited thereto.

(1)
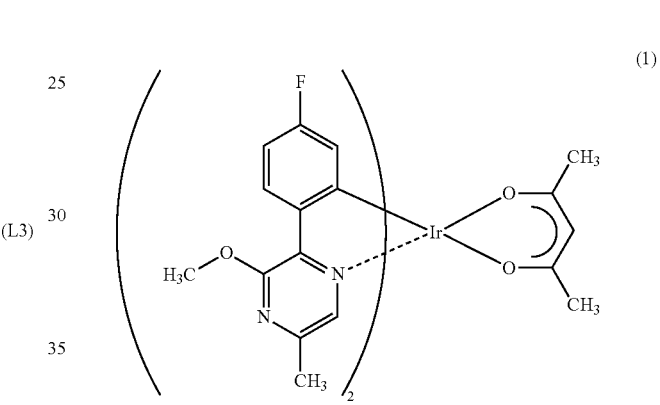

(2)
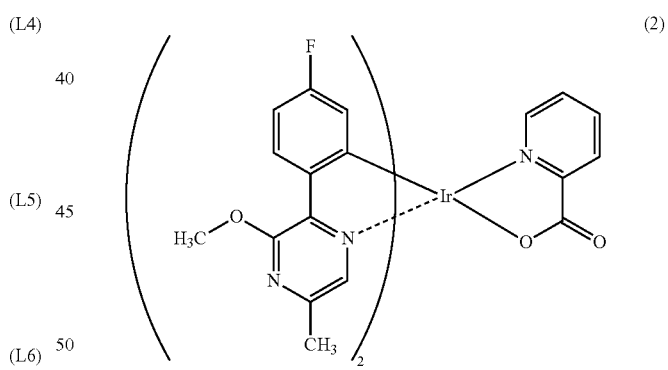

(3)
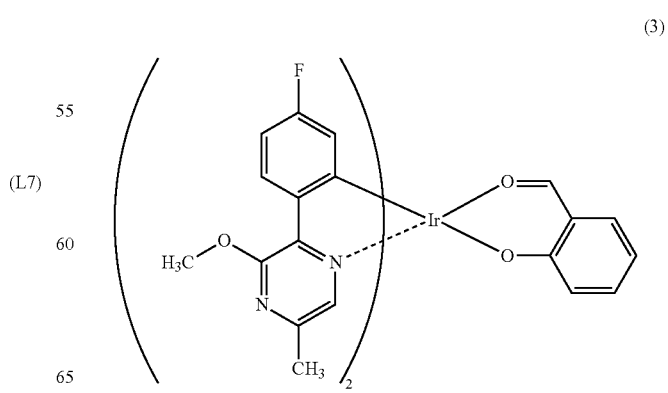

(4)
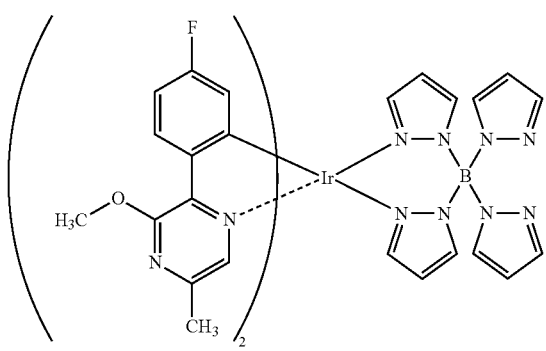
(5)
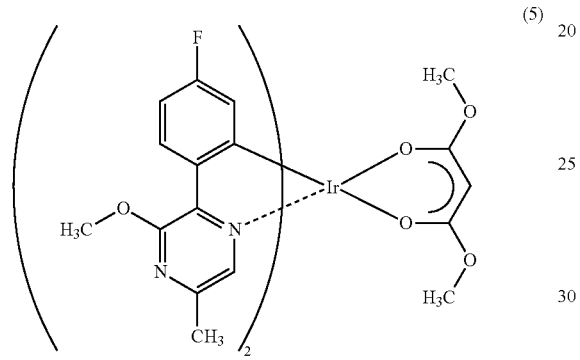
(6)
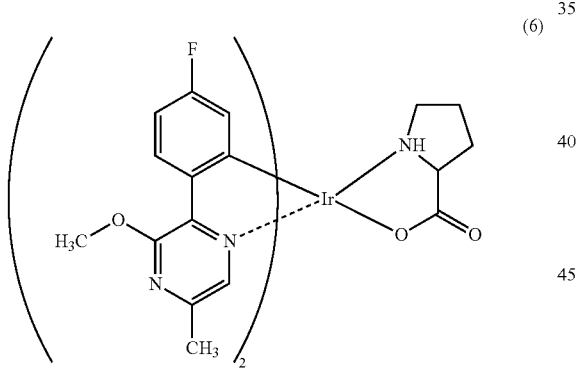
(7)
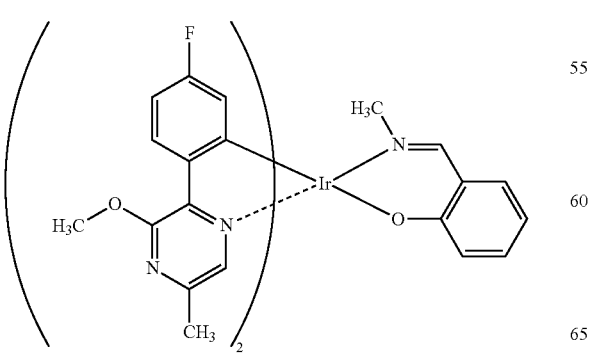
(8)
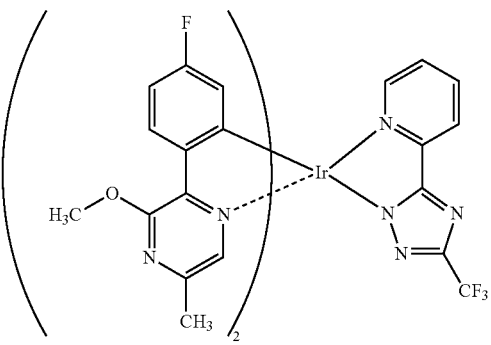
(9)
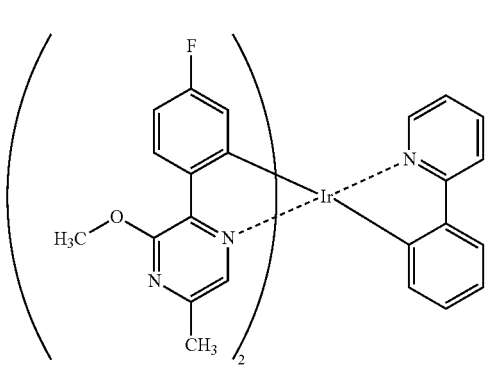
(10)
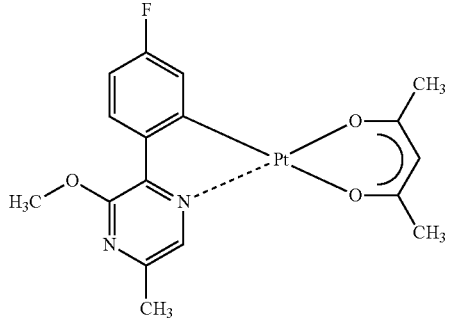
(11)

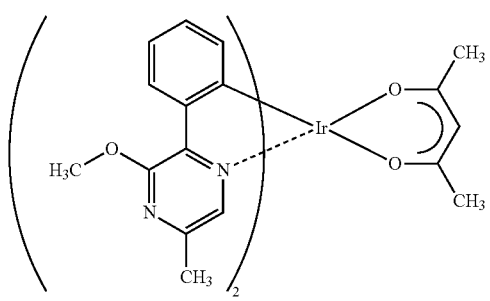 (12)
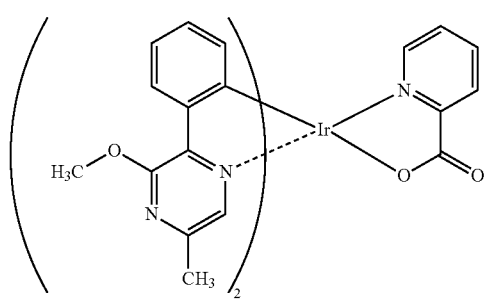 (13)
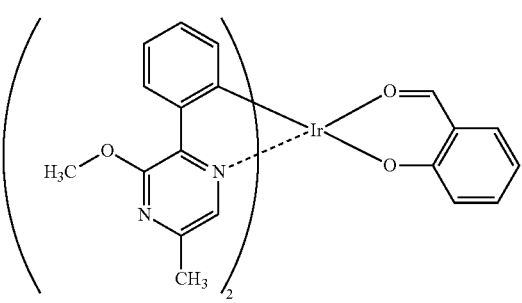 (14)
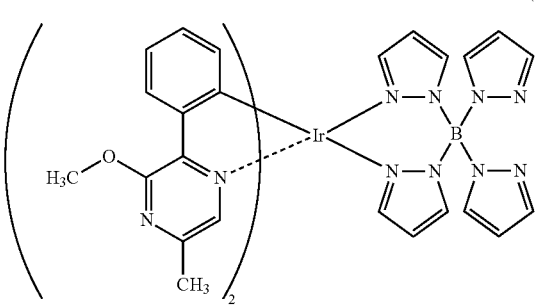 (15)
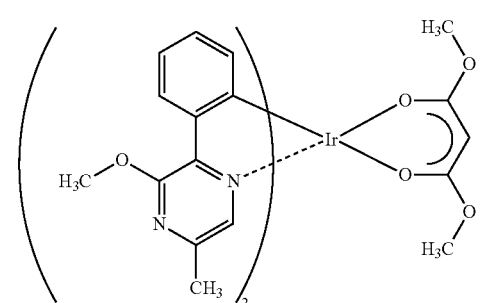 (16)
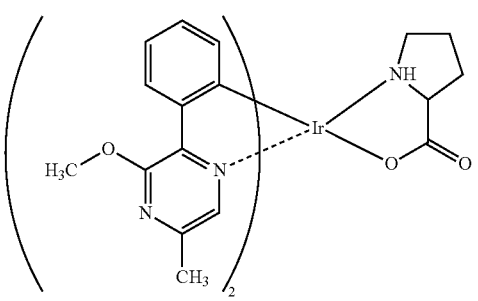 (17)
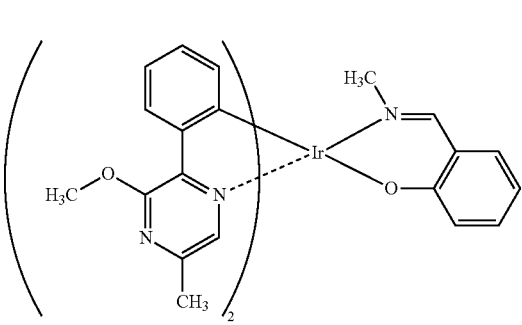 (18)
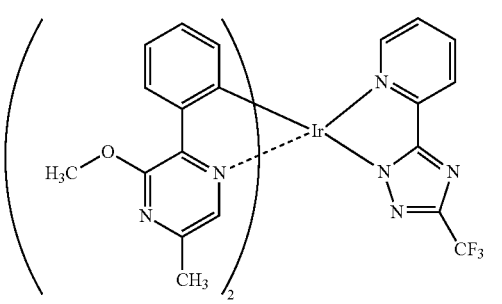 (19)
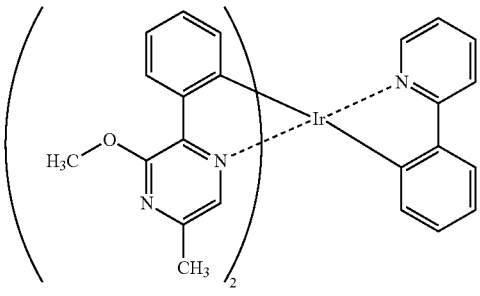 (20)
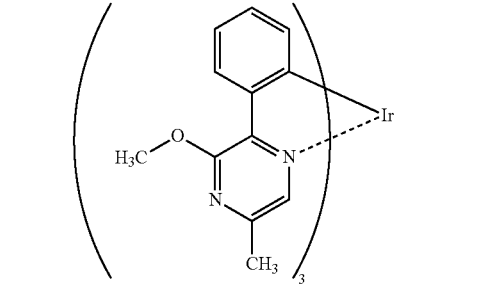 (21)

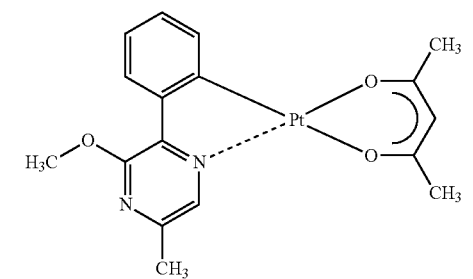
(22)
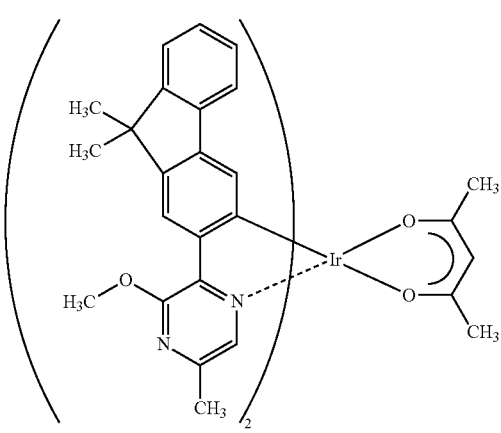
(23)
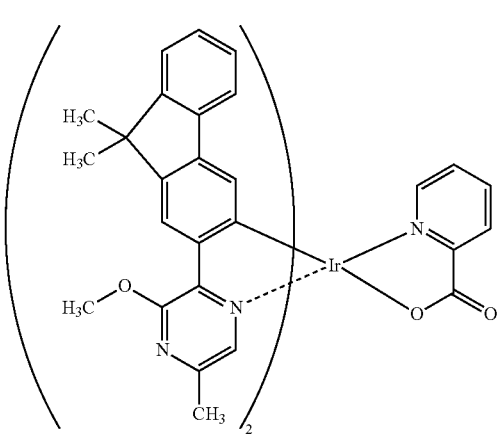
(24)
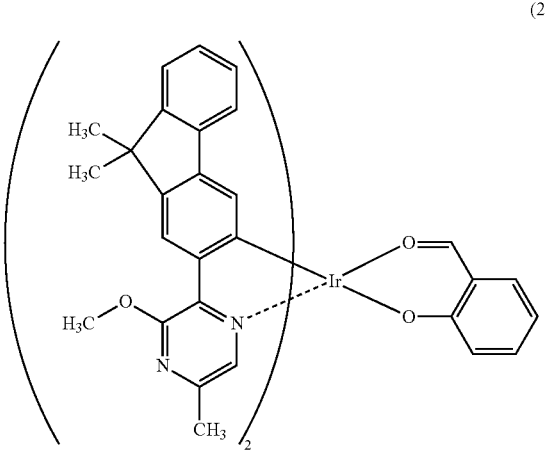
(25)
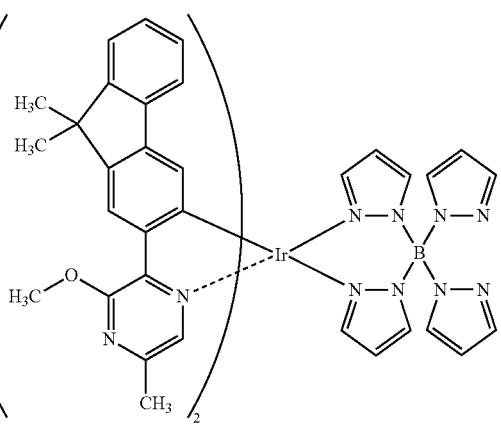
(26)
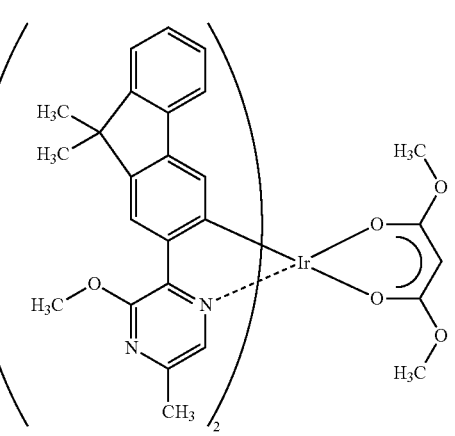
(27)
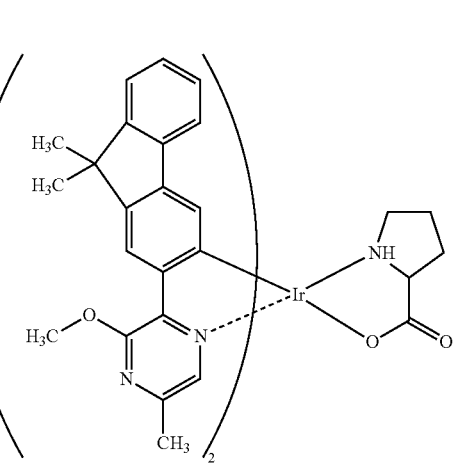
(28)

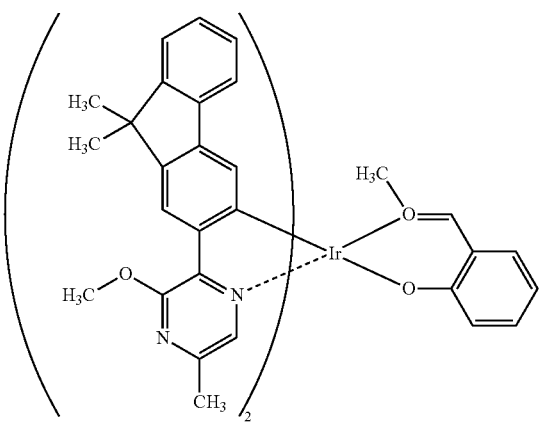
(29)
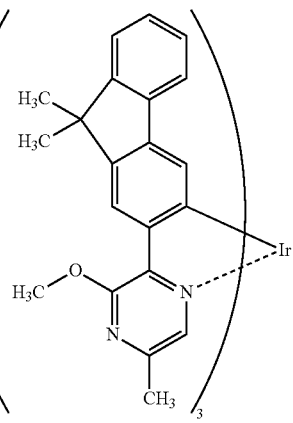
(32)
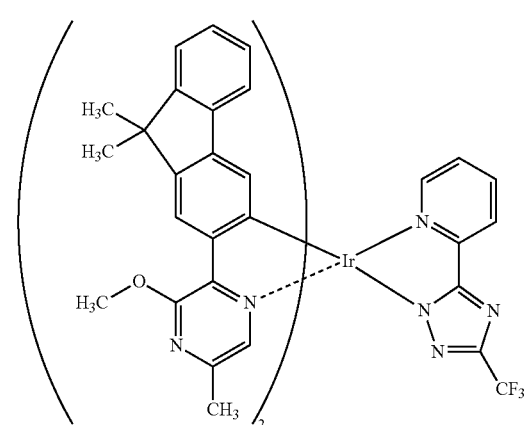
(30)
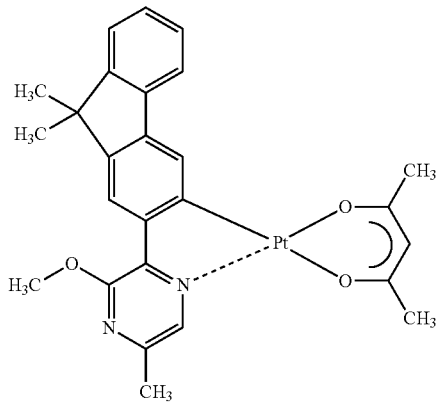
(33)
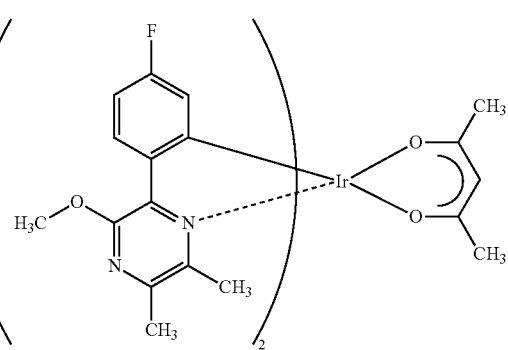
(34)
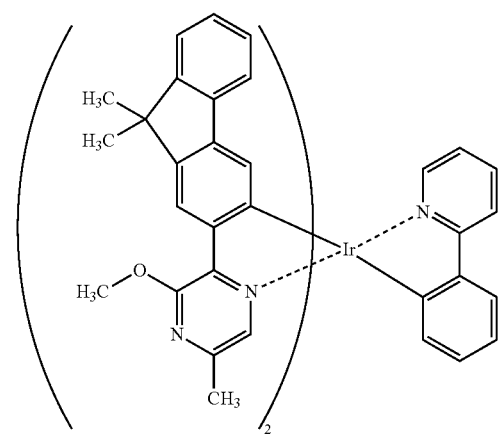
(31)
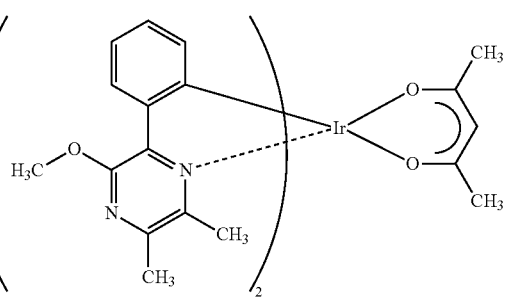
(35)

(36)
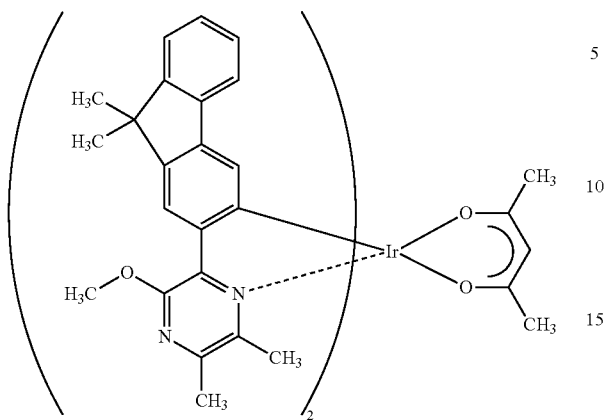
(37)
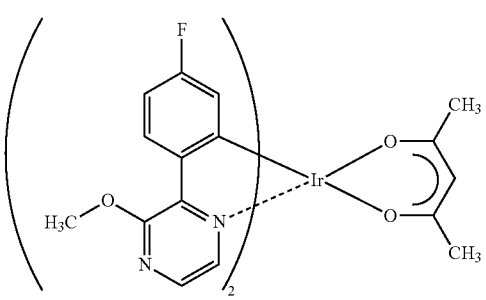
(38)
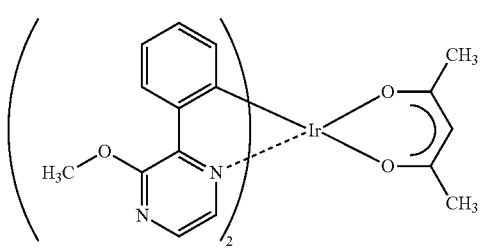
(39)
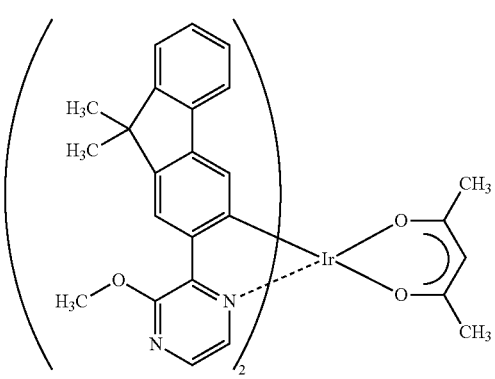
(40)
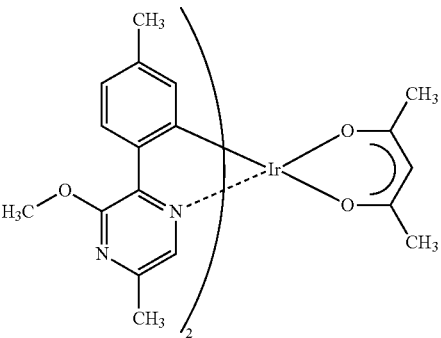
(41)
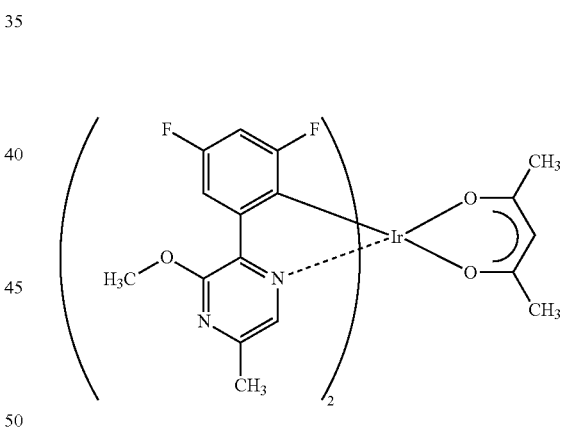
(42)
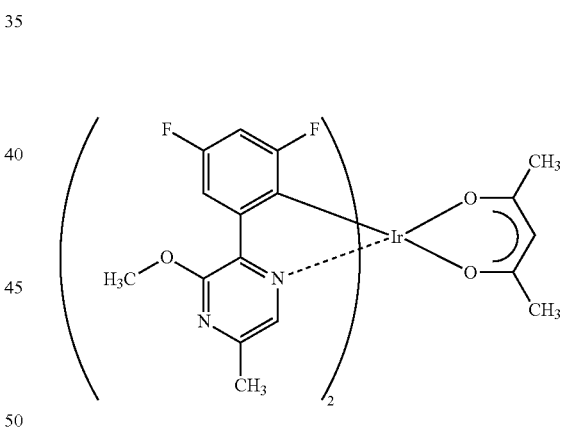
(43)
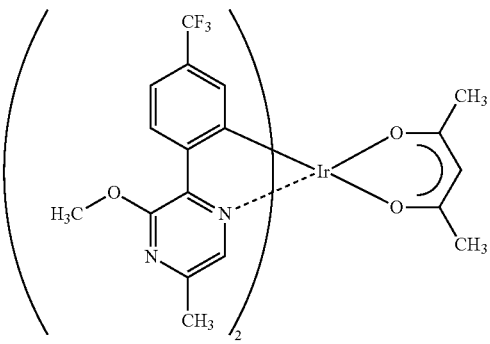

(44)

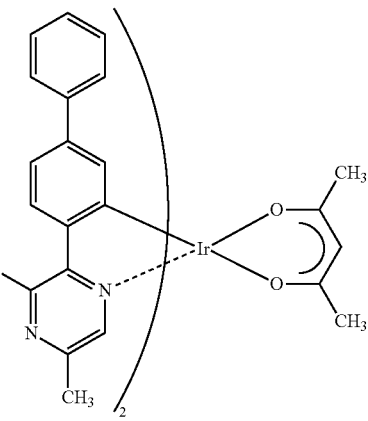

(45)

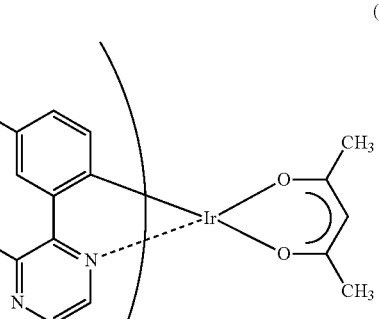

(46)

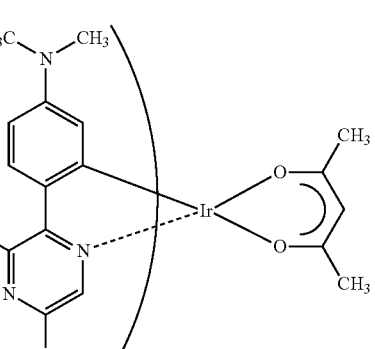

(47)

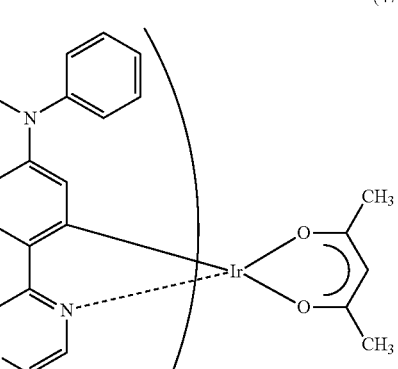

In the organometallic complexes represented by the above structural formulae (1) to (47), there can be a geometrical isomer and a stereoisomer according to the type of ligand. The organometallic complex of the present invention includes such isomers.

In addition, there are two geometrical isomers of a facial isomer and a meridional isomer as the organometallic complex represented by the structural formulae (10), (21) and (32). The organometallic complex of the present invention includes both isomers.

The foregoing organometallic complex of the present invention can be used as a photosensitizer owing to capability of intersystem crossing. Further, it can exhibit phosphorescence. Thus, the organometallic complexes of the present invention can each be used as a light-emitting material or a light-emitting substance for a light-emitting element.

(Embodiment Mode 2)

Embodiment Mode 2 will describe a mode of a light-emitting element which has the organometallic complex of the present invention described in Embodiment Mode 1, as a light-emitting substance with reference to FIG. 1.

FIG. 1 is a view showing a light-emitting element including a light-emitting layer 113 between a first electrode 101 and a second electrode 102. The light-emitting layer 113 includes such an organometallic complex of the present invention as described in Embodiment Mode 1.

By applying a voltage to such a light-emitting element, holes injected from the first electrode 101 side and electrons injected from the second electrode 102 side recombine with each other in the light-emitting layer 113 to bring the organometallic complex of the present invention to an excited state. When the organometallic complex in the excited state returns to the ground state, it emits light. As thus described, the organometallic complex of the present invention functions as a light-emitting substance of the light-emitting element. It is to be noted that, in the light-emitting element of the present Embodiment Mode 2, the first electrode 101 functions as an anode and the second electrode 102 functions as a cathode.

Here, the light-emitting layer 113 includes an organometallic complex of the present invention. The light-emitting layer 113 preferably includes, as a host, a substance which has a larger triplet excitation energy than that of the organometallic complex of the present invention and also includes, as a guest, the organometallic complex of the present invention, which is dispersedly contained. Thus, quenching of light emitted from the organometallic complex of the present invention caused depending on the concentration can be prevented. It is to be noted that the triplet excitation energy indicates an energy gap between a ground state and a triplet excited state.

There are no particular limitations on substances used to disperse an organometallic complex of the present invention (i.e., host). Specifically, an aromatic amine compound such as 4,4'-bis[N-(1-naphtyl)-N-phenylamino]biphenyl (abbreviation: NPB), 4,4'-bis[N-(9-phenanthryl)-N-phenylamino]biphenyl (abbreviation: PPB), 4,4'-bis[N-(3-methylphenyl)-N-phenylamino]biphenyl (abbreviation: TPD), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: m-MTDATA), 4,4',4''-tri(N-carbazolyl)triphenylamine (abbreviation: TCTA), 1,1-bis[4-(diphenylamino)phenyl]cyclohexane (abbreviation: TPAC), 9,9-bis[4-(diphenylamino)phenyl]fluorene (abbreviation: TPAF), 4-(9H-carbazolyl)-4'-(5-phenyl-1,3,4-oxadiazol-2-yl)triphenylamine (abbreviation: YGAO11), or N-[4-(9-carbazolyl)phenyl]-N-phenyl-9,9-dimethylfluoren-2-amine (abbreviation: YGAF) can be used. Also, a carbazole derivative such as 4,4'-di(N-carbazolyl)biphenyl (abbreviation: CBP), 1,3-bis(N-carbazolyl)benzene (abbreviation: mCP), or 1,3,5-tris(N-carbazolyl)benzene (abbreviation: TCzB) can be used. Further, a high molecular compound such as poly(4-vinyltriphenylamine) (abbreviation: PVTPA) can also be used as such an aromatic amine compound. As a carbazole derivative, a high molecular compound such as poly(N-vinylcarbazole) (abbreviation: PVK) can also be used. The triplet excitation energy of the substance serving as a host as described above is preferably larger than that of the pyrazine-based organometallic complex of the present invention.

A light-emitting element formed using the organometallic complex of the present invention has a sharp emission spectrum, and thus the light-emitting element has high color purity. Since the organometallic complex of the present invention has enriched variation of emission color of green light to red light, a light-emitting element which can emit various light of green to red, can be provided. Furthermore, since the organometallic complex of the present invention has high emission efficiency of phosphorescence, a light-emitting element with high emission efficiency can be provided.

Although there is no particular limitation on the first electrode 101, the first electrode 101 is preferably formed by using a substance which has a high work function when the first electrode 101 functions as an anode as in Embodiment Mode 2. Specifically, gold (Au), platinum (Pt), nickel (Ni), tungsten (W), chromium (Cr), molybdenum (Mo), iron (Fe), cobalt (Co), copper (Cu), palladium (Pd), and the like can be used in addition to indium tin oxide (ITO), indium tin oxide containing silicon oxide (ITSO), indium oxide containing 2 to 20 wt % zinc oxide (IZO). The first electrode 101 can be formed by, for example, a sputtering method, an evaporation method, or the like.

There is no particular limitation on a material for the second electrode 102. However, when the second electrode 102 functions as a cathode as in Embodiment Mode 2, a substance having a low work function is preferably used. Specifically, in addition to aluminum (Al) or indium (In), an alkali metal such as lithium (Li) or cesium (Cs); an alkali-earth metal such as magnesium (Mg) or calcium (Ca); a rare-earth metal such as erbium (Er) or ytterbium (Yb) or the like can be used. In addition, an alloy such as aluminum-lithium alloy (AlLi) or magnesium-silver alloy (MgAg) can also be used. The second electrode 102 can be formeed by, for example, sputtering, evaporation, or the like.

Note that a conductive composition including a conductive high molecular compound (also referred to as a conductive polymer) can be used for the first electrode 101 and the second electrode 102. When a thin film of a conductive composition is formed as each of the first electrode 101 and the second electrode 102, the thin film preferably has sheet resistance of equal to or less than 10000 Ω/square and light transmittance of equal to or higher than 70% at a wavelength of 550 nm. Note that resistance of a conductive high molecule which is included in the thin film is preferably equal to or lower than 0.1 Ω·cm.

As a conductive high molecule, so-called n electron conjugated high molecule can be used. For example, polyaniline and/or a derivative thereof, polypyrrole and/or a derivative thereof, polythiophene and/or a derivative thereof, and a copolymer of two or more kinds of those materials can be given.

Specific examples of a conjugated conductive high-molecule are given below: polypyrrole, poly(3-methylpyrrole), poly(3-butylpyrrole), poly(3-octylpyrrole), poly(3-decylpyrrole), poly(3,4-dimethylpyrrole), poly(3,4-dibutylpyrrole), poly(3-hydroxypyrrole), poly(3-methyl-4-hydroxypyrrole), poly(3-methoxypyrrole), poly(3-ethoxypyrrole), poly(3-octoxypyrrole), poly(3-carboxylpyrrole), poly(3-methyl-4-carboxylpyrrole), polyN-methylpyrrole, polythiophene, poly(3-methylthiophene), poly(3-butylthiophene), poly(3-octylthiophene), poly(3-decylthiophene), poly(3-dodecylthiophene), poly(3-methoxythiophene), poly(3-ethoxythiophene), poly(3-octoxythiophene), poly(3-carboxylthiophene), poly(3-methyl-4-carboxylthiophene), poly(3,4-ethylenedioxythiophene), polyaniline, poly(2-methylaniline), poly(2-octylaniline), poly(2-isobutylaniline), poly(3-isobutylaniline), poly(2-anilinesulfonic acid), or poly (3-anilinesulfonic acid).

One of the above-described conductive high molecular compounds can be used alone for the first electrode 101 or the second electrode 102, or an organic resin is added to such a conductive high molecular compound in order to adjust film characteristics such that it can be used as a conductive composition.

As for an organic resin, a thermosetting resin, a thermoplastic resin, or a photocurable resin may be used, as long as such a resin is compatible to a conductive high molecule or a resin can be mixed and dispersed into a conductive high molecule. For example, a polyester-based resin such as polyethylene terephthalate, polybutylene terephthalate, or polyethylene naphthalate; a polyimide-based resin such as polyimide or polyimide amide; a polyamide resin such as polyamide 6, polyamide 6,6, polyamide 12, or polyamide 11; a fluorine resin such as poly(vinylidene fluoride), polyvinyl fluoride, polytetrafluoroethylene, ethylene tetrafluoroethylene copolymer, or polychlorotrifluoroethylene; a vinyl resin such as polyvinyl alcohol, polyvinyl ether, polyvinyl butyral, polyvinyl acetate, or polyvinyl chloride; an epoxy resin; a xylene resin; an aramid resin; a polyurethane-based resin; a polyurea-based resin, a melamine resin; a phenol-based resin; polyether; an acrylic-based resin, or a copolymer of any of those resins can be given.

Further, the conductive high molecule or conductive composition may be doped with an acceptor dopant or a donor dopant so that oxidation-reduction potential of a conjugated electron in the conductive high-molecule or the conductive composition may be changed in order to adjust conductivity of the conductive high molecule or conductive composition.

As an acceptor dopant, a halogen compound, an organic cyano compound, an organic metal compound, or the like can be used. Examples of a halogen compound are chlorine, bromine, iodine, iodine chloride, iodine bromide, iodine fluoride, and the like. Lewis acid such as phosphorus pentafluoride, arsenic pentafluoride, antimony pentafluoride, boron trifluoride, boron trichloride, and boron tribromide; proton acid such as inorganic acid such as hydrochloric acid, sulfuric acid, nitric acid, phosphoric acid, fluoroboric acid, hydrofluoric acid, and perchloric acid and organic acid such as organic carboxylic acid and organic sulfonic acid can be used. As the organic carboxylic acid and the organic sulfonic acid, the above-described carboxylic acid compounds or sulfonic acid compounds can be used. As the organic cyano compound, a compound in which two or more cyano groups are included in a conjugated bond can be used. For example, there are tetracyanoethylene, tetracyano ethylene oxide, tetracyanobenzene, tetracyanoquinodimethane, tetracyano azanaphthalene, and the like.

As the donor dopant, there are alkali metal, alkaline-earth metal, a quaternary amine compound, and the like.

Further, a thin film used for the first electrode 101 or the second electrode 102 can be formed by a wet process using a solution in which the conductive high molecule or the conductive composition is dissolved in water or an organic solvent (e.g., an alcohol solvent, a ketone solvent, an ester solvent, a hydrocarbon solvent, or an aromatic solvent).

There is no particular limitation on the solvent in which the conductive high molecule or the conductive composition is dissolved as long as the above-described conductive high molecule and the high molecular resin compound such as an organic resin are dissolved. For example, the conductive composition may be dissolved in a single solvent or a mixed solvent of the following: water, methanol, ethanol, propylene carbonate, N-methylpyrrolidone, dimethylformamide, dimethylacetamide, cyclohexanone, acetone, methyletylketone, methylisobutylketone, toluene, and/or the like.

Formation of a film using a solution in which the conductive high molecule or conductive composition is dissolved in a solvent can be performed by a wet process, such as an application method, a coating method, a droplet discharge method (also referred to as an inkjet method), or a printing method. The solvent may dried with thermal treatment or may be dried under reduced pressure. In the case where the organic resin is a thermosetting resin, heat treatment may be performed further. In the case where the organic resin is a photocurable resin, light irradiation treatment may be performed.

In order to extract emitted light to the outside, it is preferable that one or both of the first electrode 101 and the second electrode 102 be an electrode formed using a conductive film through which visible light is transmitted, such as ITO, or an electrode formed with a thickness of several to several tens of nm such that visible light can be transmitted.

In addition, a hole-transporting layer 112 may be provided between the first electrode 101 and the light-emitting layer 113 as shown in FIG. 1. Here, the hole-transporting layer is a layer that has a function of transporting holes injected from the first electrode 101 to the light-emitting layer 113. The hole-transporting layer 112 is provided to keep the first electrode 101 away from the light-emitting layer 113 in this way; thus, quenching of light due to a metal can be prevented. However, the hole-transporting layer 112 is not necessarily provided.

There is no particular limitation on the substance for forming the hole-transporting layer 112. Specifically, an aromatic amine compound such as 4,4'-bis[N-(1-napthyl)-N-phenylamino]biphenyl (abbreviation: NPB), 4,4'-bis[N-(9-phenanthryl)-N-phenylamino]biphenyl (abbreviation: PPB), 4,4'-bis[N-(3-methylphenyl)-N-phenylamino]biphenyl (abbreviation: TPD), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: m-MTDATA), 4,4',4''-tri(N-carbazolyl)triphenylamine (abbreviation: TCTA), 1,1-bis[4-(diphenylamino)phenyl]cyclohexane (abbreviation: TPAC), 9,9-bis[4-(diphenylamino)phenyl]fluorene (abbreviation: TPAF), 4-(9-carbazolyl)-4'-(5-phenyl-1,3,4-oxadiazol-2-yl)triphenylamine (abbreviation: YGAO11), or N-[4-(9-carbazolyl)phenyl]-N-phenyl-9,9-dimethylfluoren-2-amine (abbreviation: YGAF) can be used. Also, a carbazole derivative such as 4,4'-di(N-carbazolyl)biphenyl (abbreviation: CBP), 1,3-bis(N-carbazolyl)benzene (abbreviation: mCP), or 1,3,5-tris(N-carbazolyl)benzene (abbreviation: TCzB) can be used. Further, a high molecular compound such as poly(4-vinyltriphenylamine) (abbreviation: PVTPA) can also be used as such an aromatic amine compound. As a carbazole derivative, a high molecular compound such as poly(N-vinylcarbazole) (abbreviation: PVK) can also be used. The triplet excitation energy of the substance used for the hole-transporting layer 112 is preferably larger than that of the pyrazine-based organometallic complex.

It is to be noted that the hole-transporting layer 112 may have a multilayer structure formed of two or more layers stacked together. In addition, the hole-transporting layer 112 may also be formed by mixing two or more types of substances.

Moreover, an electron-transporting layer 114 may be provided between the second electrode 102 and the light-emitting layer 113 as shown in FIG. 1. Here, the electron-transporting layer is a layer which has a function of transporting electrons injected from the second electrode 102 to the light-emitting layer 113. In such a manner, the electron-transporting layer 114 is provided to separate the second electrode 102 from the light-emitting layer 113, whereby quenching of light-emission due to a metal can be prevented. Note that the electron-transporting layer 114 is not always necessary.

There is no particular limitation on a substance for forming the electron-transporting layer 114. Specifically, a heteroaromatic compound such as 9-[4-(5-phenyl-1,3,4-oxadiazol-2-yl)phenyl]carbazole (abbreviation: CO11), 1,3-bis[5-(p-tert-buthylphenyl)-1,3,4-oxadiazol-2-yl]benzene (abbreviation: OXD-7), 2-(4-biphenylyl)-5-(4-tert-butylphenyl)-1,3,4-oxadiazole (abbreviation: PBD), 2,2',2''-(1,3,5-benzenetriyl)tris (1-phenyl-1H-benzimidazole) (abbreviation: TPBI), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), 9,9',9''-[1,3,5-triazine-2,4,6-triyl]tricarbazole (abbreviation: TCzTRZ), 2,2',2''-(1,3,5-benzenetriyl)tris(6,7-dimethyl-3-phenylquinoxaline) (abbreviation: TriMeQn), 9,9'-(quinoxaline-2,3-diyldi-4,1-phenylene)di(9H-carbazole) (abbreviation: CzQn), 3,3',6,6'-tetraphenyl-9,9'-(quinoxaline-2,3-diyldi-4,1-phenylene)di(9H-carbazole) (abbreviation: DCzPQ), bathophenanthroline (abbreviation: BPhen), or bathocuproine (abbreviation: BCP) can be used. A metal complex such as is bis(2-methyl-8-quinolinolato)(4-phenylphenolato)aluminum(III) (abbreviation: BAlq), tris[2-(2-hydroxyphenyl)-5-phenyl-1,3,4-oxadiazolato]aluminum (III) (abbreviation: Al(OXD)$_3$), tris(2-hydroxyphenyl-1-phenyl-1H-benzimidazolato)aluminum(III) (abbreviation: Al(BIZ)$_3$), bis[2-(2-hydroxyphenyl)benzothiazolato]zinc(II) (abbreviation: Zn(BTZ)$_2$), or bis[2-(2-hydroxyphenyl)benzoxazolato]zinc(II) (abbreviation: Zn(PBO)$_2$) can be used. Further, a high molecular compound such as poly(2,5-pyridine-diyl) (abbreviation: PPy) can also be used as such a heteroaromatic compound. As a metal complex, metal complex high molecular compounds as disclosed as in the following reference can also be used (TAO et al., C—H BOND ACTIVATION BY A FERRIC METHOXIDE COMPLEX: MODELING THE RATE-DETERMINING STEP IN THE MECHANISM OF LIPDXYGENASE, APPL. PHYS. LETT. (APPLIED PHYSICS LETTERS, vol. 70, No. 12, 24 Mar. 1997, pages 1503-1505.). Note that the triplet excitation energy of the substance used for the electron-transporting layer 114 described above is preferably larger than that of the pyrazine-based organometallic complex.

Note that the electron-transporting layer 114 may have a multilayer structure in which two or more layers are stacked. In addition, the electron-transporting layer 114 may also be formed by mixing two or more types of substances.

Further, a hole-injecting layer 111 may be provided between the first electrode 101 and the hole-transporting layer 112 as shown in FIG. 1. Here, the hole-injecting layer is a layer that has a function of assisting injection of holes from an electrode functioning as an anode to the hole-transporting layer 112. Note that the hole-injecting layer 111 is not always necessary.

There is no particular limitation on the substance used for the hole-injection layer 111; a metal oxide such as vanadium oxide, niobium oxide, tantalum oxide, chromium oxide, molybdenum oxide, tungsten oxide, manganese oxide, rhenium oxide, ruthenium oxide, or the like can be used. In addition, a phthalocyanine compound such as phthalocyanine (abbreviation: $H_2Pc$), copper phthalocyanine (abbreviation: CuPc), or the like can also be used. In addition, the substances for forming the hole-transporting layer 112 as described above can also be used. Further, a high molecular compound such as a mixture of poly(ethylenedioxythiophene) and poly (styrenesulfonic acid) (abbreviation: PEDOT/PSS) can also be used.

A composite material of an organic compound and an electron acceptor may be used for the hole-injecting layer 111. Such a composite material is superior in a hole-injecting property and a hole-transporting property since holes are generated in the organic compound by the electron acceptor. In this case, the organic compound is preferably a material excellent in transporting the generated holes. Specifically, the above-described substances used for the hole-transporting layer 112 (such as aromatic amine compounds) can be used. As the electron acceptor, a substance having an electron accepting property to the organic compound may be used. Specifically, transition metal oxide is preferable and examples thereof include vanadium oxide, niobium oxide, tantalum oxide, chromium oxide, molybdenum oxide, tungsten oxide, manganese oxide, rhenium oxide, ruthenium oxide, and the like. Lewis acid such as iron(III) chloride or aluminum(III) chloride can also be used. In addition, an organic compound such as 7,7,8,8-tetracyano-2,3,5,6-tetrafluoroquinodimethane (abbrev.: F4-TCNQ) can also be used.

Note that the hole-injecting layer 111 may have a multilayer structure in which two or more layers are stacked. In addition, the hole-transporting layer 112 may also be formed by mixing two or more types of substances.

In addition, as shown in FIG. 1, an electron-injecting layer 115 may be provided between the second electrode 102 and the electron-transporting layer 114. Here, the electron-injecting layer is a layer which has a function of assisting injection of electrons from the electrode functioning as a cathode to the electron-transporting layer 114. Note that the electron-injecting layer 115 is not always necessary.

There is no particular limitation on the substance used for the electron-injecting layer 115. An alkali metal compound or an alkaline earth metal compound such as lithium fluoride, cesium fluoride, calcium fluoride, or lithium oxide can be used. In addition, a rare earth metal compound such as erbium fluoride can also be used. In addition, the substance for the electron-transporting layer 114 as described above can also be used.

Alternatively, a composite material which is formed by combining an organic compound and an electron donor may be used for the electron-injecting layer 115. Such a composite material is superior in an electron-injecting property and an electron-transporting property since electrons are generated in the organic compound by the electron donor. In this case, for the organic compound, it is preferable that it be a material that excels in the transportation of generated electrons; specifically, any of the substances (the metal complexes, the heteroaromatic compounds, and the like) given above that are used to form the electron-transporting layer 114 can be used, for example. As the electron donor, a substance showing an electron donating property to the organic compound may be used. Specifically an alkali metal, an alkali-earth metal or a rare earth metal is preferable, and for example, lithium, cesium, magnesium, calcium, erbium, or ytterbium, can be given. Further, alkali metal oxide or alkaline-earth metal oxide is preferable, and for example, lithium oxide, calcium oxide, barium oxide, or the like can be given. In addition, an alkali metal compound or an alkaline earth metal compound such as lithium oxide, calcium oxide, barium oxide, or cesium carbonate can be used. Further, Lewis base such as magnesium oxide or an organic compound such as tetrathiafulvalene (abbreviation: TTF) can also be used.

In the foregoing light-emitting element of the present invention, each of the hole-injecting layer 111, the hole-transporting layer 112, the light-emitting layer 113, the electron-transporting layer 114, and the electron-injecting layer 115 may be formed by any method, for example, an evaporation method, an inkjet method, an application method, or the like. In addition, the first electrode 101 or the second electrode 102 may be foamed by any method, for example, a sputtering method, an evaporation method, an inkjet method, an application method, or the like.

(Embodiment Mode 3)

A light-emitting element of the present invention may have a plurality of light-emitting layers. For example, white light can be obtained by providing a plurality of light-emitting layers and mixing light emitted from each of the light-emitting layers. Accordingly, white color light emission can be obtained for example. In Embodiment Mode 3, a light-emitting element having a plurality of light-emitting layers is described with reference to FIG. 2.

Figure 2:
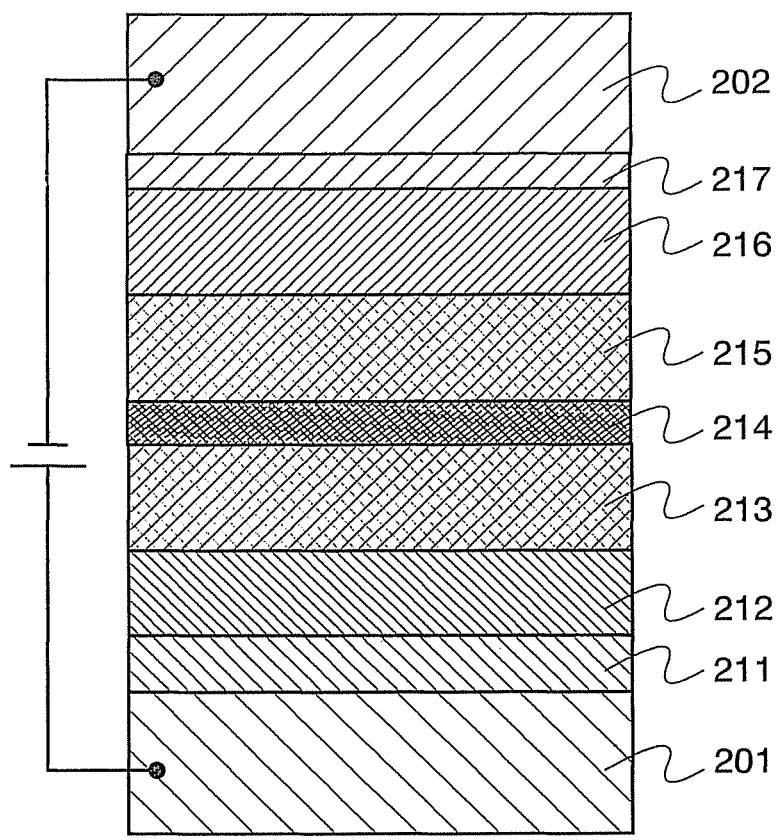
FIG. 2 illustrates a structure of a light-emitting element using an organometallic complex according to an aspect of the present invention.

In FIG. 2, a first light-emitting layer 213 and a second light-emitting layer 215 are provided between a first electrode 201 and a second electrode 202. Mixed light of light emitted from the first light-emitting layer 213 and light emitted from the second light-emitting layer 215 can be obtained. A separation layer 214 is preferably formed between the first light-emitting layer 213 and the second light-emitting layer 215.

When voltage is applied such that the potential of the first electrode 201 is higher than the potential of the second electrode 202, current flows between the first electrode 201 and the second electrode 202, and holes and electrons are recombined in the first light-emitting layer 213, the second light-emitting layer 215, or the separation layer 214. The generated excitation energy is distributed to the first light-emitting layer 213 and the second light-emitting layer 215 to bring each of a first light-emitting substance contained in the first light-emitting layer 213 and a second light-emitting substance contained in the second light-emitting layer 215 to an excited state. The excited first and second light-emitting substances emit light while returning to ground states.

The first light-emitting layer 213 contains the first light-emitting substance typified by a fluorescent substance such as perylene, 2,5,8,11-tetra(tert-butyl)perylene (abbreviation: TBP), 4,4'-bis(2,2-diphenylvinyl)biphenyl (abbreviation: DPVBi), 4,4'-bis[2-(N-ethylcarbazol-3-yl)vinyl]biphenyl (abbreviation: BCzVBi), bis(2-methyl-8-quinolinolato)(4-phenylphenolato)aluminum (abbreviation: BAlq), or bis(2-methyl-8-quinolinolato)galliumchloride (abbreviation: $Gamq_2Cl$), or a phosphorescent substance such as bis{2-[3,5-bis(trifluoromethyl)phenyl]pyridinato-N,$C^{2'}$}iridium(III) picolinate (abbreviation Ir($CF_3$ppy)$_2$(pic)), bis[2-(4,6-difluorophenyl)pyridinato-N,$C^{2'}$]iridium(III)acetylacetonate (abbreviation: FIr(acac)), bis[2-(4,6-difluorophenyl)pyridinato-N,$C^{2'}$]iridium(III)picolinate (abbreviation FIrpic), or bis[2-(4,6-difuluorophenyl)pyridinato-N,$C^{2'}$]iridium(III) tetra(1-pyrazolyl)borate (abbreviation: FIr6), from which light emission with a peak between 450 nm and 510 nm in an emission spectrum (i.e., blue light to blue green light) can be obtained. In addition, when the first light-emitting substance is a fluorescent compound, the first light-emitting layer 213 preferably has a structure in which a substance having a larger singlet excited energy than the first light-emitting substance is used as a first host and the first light-emitting substance is dispersedly contained as a guest. Further, when the first light-emitting substance is a phosphorescent compound, the light-emitting layer 213 preferably has a structure in which a substance having a larger triplet excited energy than the first light-emitting substance is used as a first host and the first light-emitting substance is dispersedly contained as a guest. As the first host, 9,10-di(2-naphthyl)anthracene (abbreviation: DNA), 2-tert-butyl-9,10-di(2-naphthyl)anthracene (abbreviation: t-BuDNA) or the like can be used as well as NPB, CBP, TCTA or the like. It is noted that the singlet exited energy is energy difference between a ground state and a singlet excited state, and the triplet exited energy is energy difference between a ground state and a triplet excited state.

On the other hand, the second light-emitting layer 215 includes an organometallic complex of the present invention and can exhibit light emission of green to red. The second light-emitting layer 215 may have the same structure as the light-emitting layer 113 described in Embodiment Mode 2.

In addition, the separation layer 214 can be specifically formed of TPAQn, NPB, CBP, TCTA, Znpp$_2$, ZnBOX or the like described above. The separation layer 214 is provided in this manner, and therefore a defect that emission intensity of only one of the first light-emitting layer 213 and the second light-emitting layer 215 is stronger than that of the other thereof can be prevented. However, the separation layer 214 is not necessarily provided, and it may be provided as appropriate such that the ratio between emission intensities of the first light-emitting layer 213 and the second light-emitting layer 215 can be adjusted.

In Embodiment Mode 3, an organometallic complex of the present invention is used for the second light-emitting layer 215, and another light-emitting substance is used for the first light-emitting layer 213; however, the organometallic complex of the present invention may be used for the first light-emitting layer 213, and another light-emitting substance is used for the second light-emitting layer 215.

In Embodiment Mode 3, a light-emitting element including two light-emitting layers is described as shown in FIG. 2; however, the number of the light-emitting layers is not limited to two, and may be three, for example. Light emission from each light-emitting layer may be mixed. As a result, white color emission can, for example, be obtained.

It is to be noted that, the first electrode 201 may have the same structure as the first electrode 101 described in the preceding Embodiment Mode 2. In addition, the second electrode 202 may have a structure similar to the second electrode 102 described in Embodiment Mode 2.

In Embodiment Mode 3, as shown in FIG. 2, the hole-injecting layer 211, the hole-transporting layer 212, the electron-transporting layer 216, and the electron-injecting layer 217 are provided; however, also to structures of these layers, the structures of the respective layers described in Embodiment Mode 2 may be applied. However, these layers are not necessarily provided and may be provided according to element characteristics.

(Embodiment Mode 4)

Embodiment Mode 4 exemplifies a light-emitting element which includes a plurality of light-emitting layers, which has a different element structure from that in Embodiment Mode 3, and in which light is emitted from each light-emitting layer.

Therefore, also in Embodiment Mode 4, light which is the combination of a plurality of light can be obtained. In other words, white color light emission can be obtained, for example. Hereinafter, description is made with reference to FIG. 3.

Figure 3:
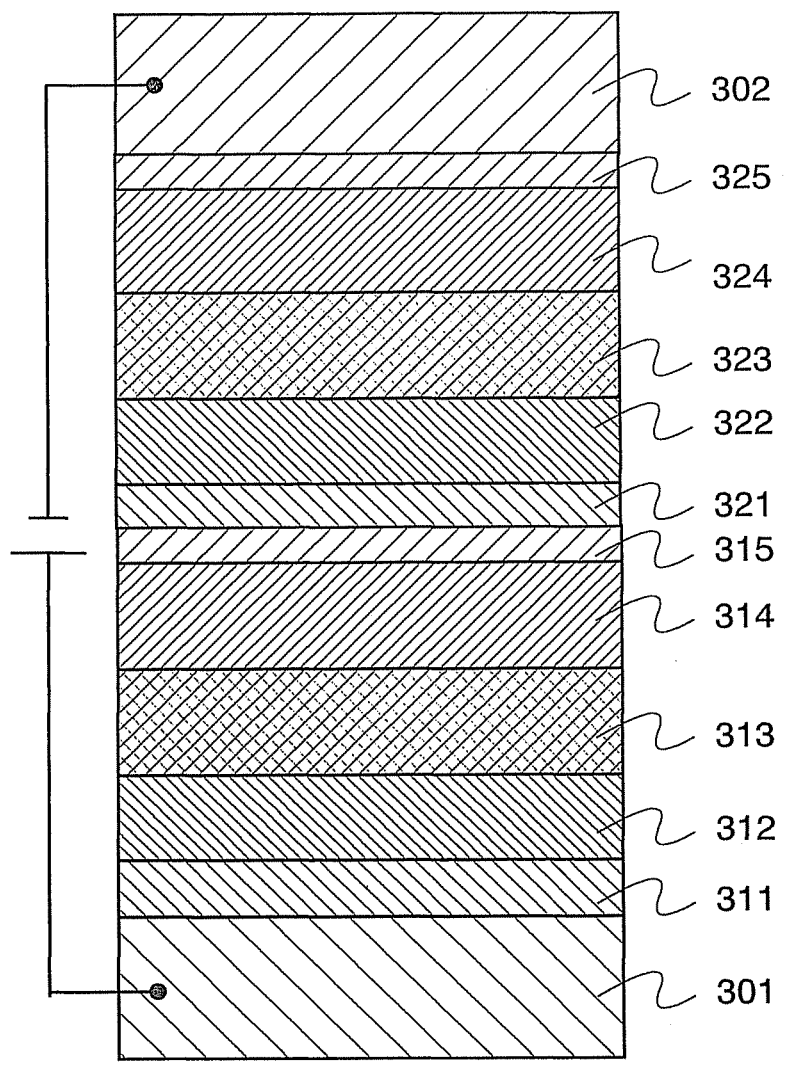
FIG. 3 illustrates a structure of a light-emitting element using an organometallic complex according to an aspect of the present invention.

In the light-emitting element of FIG. 3, a first light-emitting layer 313 and a second light-emitting layer 323 are provided between a first electrode 301 and a second electrode 302. An N layer 315 and a P layer 321 as charge generating layers are provided between the first light-emitting layer 313 and the second light-emitting layer 323.

The N layer 315 is a layer for generating electrons, and the P layer 321 is a layer for generating holes. When a voltage is applied such that the potential of the first electrode 301 is higher than that of the second electrode 302, holes injected from the first electrode 301 and electrons injected from the N layer 315 are recombined in the first light-emitting layer 313, and thus a first light-emitting substance included in the first light-emitting layer 313 emits light. Further, electrons injected from the second electrode 302 and holes injected from the P layer 321 are recombined in the second light-emitting layer 323, and thus a second light-emitting substance included in the second light-emitting layer 323 emits light.

The first light-emitting layer 313 may have the same structure as the first light-emitting layer 213 in Embodiment Mode 3, and light with a peak of emission spectrum (i.e., blue light to blue green light) between 450 nm and 510 nm can be emitted. The second light-emitting layer 323 may have the same structure as the second light-emitting layer 215 in Embodiment Mode 3, and includes an organometallic complex of the present invention and green light to red light can be obtained.

The N layer 315 is a layer for generating electrons and thus may be formed using a composite material in which the organic compound and the electron donor described in Embodiment Mode 2 are combined. By adopting such a structure, electrons can be injected to the first light-emitting 313 side.

Since the P layer 321 is a layer for generating holes, it may be formed using a composite material in which the organic compound and the electron donor described in Embodiment Mode 2 are combined. By adopting such a structure, holes can be injected to the second light-emitting 323 side. For the P layer 321, metal oxide having an excellent hole-injecting property, such as molybdenum oxide, vanadium oxide, ITO, or ITSO, can be used.

Here, Embodiment Mode 4 describes a light-emitting element in which the two light-emitting layers are provided as shown in FIG. 3; however, the number of light-emitting layers is not limited to two. For example, three light-emitting layers may be provided. Light emission from each light-emitting layer may be mixed. As a result, white color emission can, for example, be obtained.

The first electrode 301 may have a similar structure to the first electrode 101 of Embodiment Mode 2. In addition, the second electrode 302 may have the same structure as the second electrode 102 described in Embodiment Mode 2.

In Embodiment Mode 4, as shown in FIG. 3, a hole-injecting layer 311, hole-transporting layers 312 and 322, electron-transporting layers 314 and 324, and an electron-injecting layer 325 are provided. As to these layers, the structures of the respective layers described in Embodiment Mode 2 may also be applied. However, these layers are not necessarily provided and may be provided according to element characteristics.

(Embodiment Mode 5)

Embodiment Mode 5 will describe a mode of a light-emitting element using the organometallic complex of the present invention as a sensitizer, with reference to FIG. 1.

FIG. 1 shows a light-emitting element including a light-emitting layer 113 between a first electrode 101 and a second electrode 102. The light-emitting layer 113 contains such an organometallic complex of the present invention as described in Embodiment Mode 1, and a fluorescent compound which can emit light with a longer wavelength than the organometallic complex of the present invention.

In the light-emitting element like this, holes injected from the first electrode 101 and electrons injected from the second electrode 102 are recombined in the light-emitting layer 113 to bring the fluorescent compound to be in an excited state. The fluorescent compound in an excited state emits light while returning to the ground state. In this case, the organometallic complex of the present invention acts as a sensitizer for the fluorescent compound to make more molecules of the fluorescent compound be in the singlet excited state. As noted above, a light-emitting element with good light emission efficiency can be obtained by using the organometallic complex according to the present invention as a sensitizer. It is to be noted that the first electrode 101 functions as an anode and the second electrode 102 functions as a cathode in the light-emitting element in Embodiment Mode 5.

Here, the light-emitting layer 113 includes an organometallic complex of the present invention, and a fluorescent compound which can emit light with a longer wavelength than the organometallic complex of the present invention. The light-emitting layer 113 may preferably have a structure in which a substance that has a larger singlet excitation energy than the fluorescent compound and has a larger triplet excitation energy than the organometallic complex of the present invention is used as a host, and the organometallic complex of the present invention and the fluorescent compound are dispersedly contained as a guest.

There is no particular limitation on a substance (i.e., host) used for dispersing the organometallic complex of the present invention and the fluorescent compound, and a substance which is used as a host in Embodiment Mode 2, or the like can be used.

In addition, there is also no particular limitation on the fluorescent complex; however, a compound which can exhibit emission of red light to infrared light is preferable, for example, 4-dicyanomethylene-2-isopropyl-6-[2-(1,1,7,7-tetramethyljulolidin-9-yl)ethenyl]-4H-pyran (abbreviation: DCJTI), magnesium phthalocyanine, magnesium porphyrin, phthalocyanine and the like are preferable.

Note that the first electrode 101 and the second electrode 102 may both have the same structure as the first electrode and the second electrode in Embodiment Mode 2, respectively.

In Embodiment Mode 5, as shown in FIG. 1, the hole-injecting layer 111, the hole-transporting layer 112, the electron-transporting layer 114, and the electron-injecting layer 115 are provided; also to these layers, the structures of the respective layers described in Embodiment Mode 2 may be applied. However, these layers are not necessarily provided and may be provided according to element characteristics.

The foregoing light-emitting element can emit light highly efficiently by using the organometallic complex of the present invention as a sensitizer.

(Embodiment Mode 6)

Figure 4A:
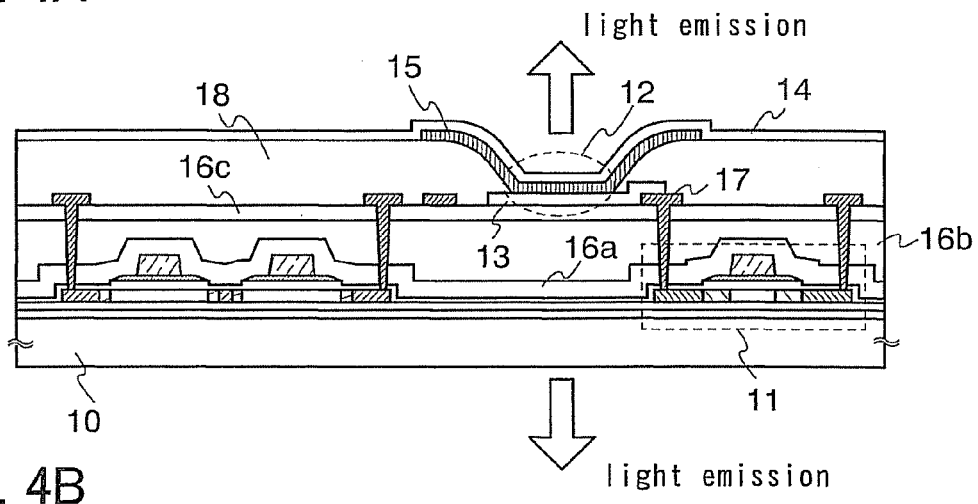
FIGS. 4A to 4C each illustrate a light-emitting device using a light-emitting element according to an aspect of the present invention.
Figure 4B:
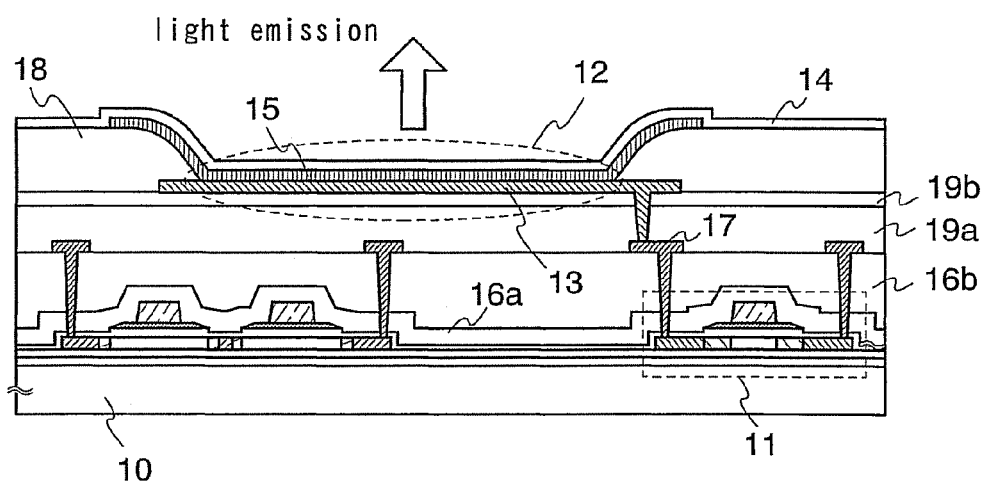
Figure 4C:
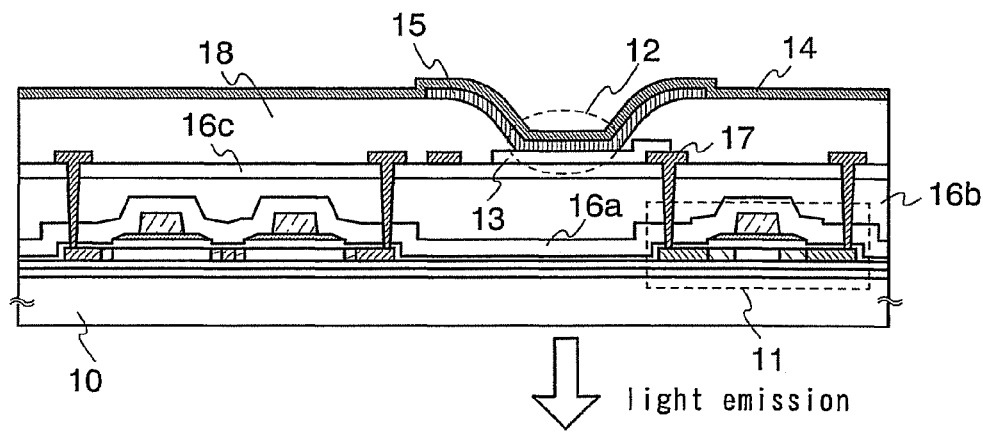

In Embodiment Mode 6, modes of light-emitting devices including the light-emitting element of the present invention are explained with reference to FIGS. 4A to 4C. FIGS. 4A to 4C show cross-sectional views of the light-emitting devices.

In FIGS. 4A to 4C, a portion surrounded by dotted lines of a rectangular shape is a transistor 11 which is provided to drive a light-emitting element 12 of the present invention. The light-emitting element 12 is a light-emitting element of the present invention in which a layer 15 including a light-emitting layer is formed between a first electrode 13 and a second electrode 14, and the light-emitting layer includes an organometallic complex of the present invention. Specifically, the light-emitting element 12 has the structure as shown in Embodiment Mode 2. A drain region of the transistor 11 and the first electrode 13 are electrically connected to each other by a wiring 17 that runs through a first interlayer insulating film 16 (16a, 16b, and 16c). The light-emitting element 12 is isolated from other light-emitting elements provided adjacent to the light-emitting element 12 by a partition layer 18. The light-emitting device having such a structure of the present invention is provided over a substrate 10 in Embodiment Mode 6.

Note that each of the transistors 11 shown in FIGS. 4A to 4C is a top gate type in which a gate electrode is provided on a side opposite to a substrate, regarding the semiconductor layer as a center. However, a structure of the transistor 11 is not particularly limited, and a bottom gate type may also be employed, for example. Further, in the case of a bottom-gate structure, a TFT in which a protective film is formed over the channel-forming semiconductor layer (a channel protection type TFT) can be used, or a TFT in which a part of the channel-forming semiconductor layer is concave (a channel etch type TFT) can also be used.

The semiconductor layer included in the transistor 11 may be either of a crystalline semiconductor or an amorphous semiconductor. Further, it may be semi-amorphous or the like.

Note that the semiamorphous semiconductor is as follows. A semi-amorphous semiconductor is a semiconductor having an intermediate state between an amorphous structure and a crystalline structure (including single crystal and polycrystal) and a third state which is stable in free energy. It further includes a crystalline region having a short range order and lattice distortion. A Raman spectrum derived from L-O phonon is shifted to a lower wavenumber side than 520 cm$^{-1}$. In X-ray diffraction, diffraction peaks of (111) and (220) due to a Si crystal lattice are observed. Hydrogen or halogen of at least 1 atomic % is contained to terminate a dangling bond. It is also referred to as a microcrystalline semiconductor. The semiamorphous semiconductor is as follows. A semi-amorphous semiconductor is a semiconductor having an intermediate state between an amorphous structure and a crystalline structure (i is formed by decomposing a gas including silicon with glow discharge decomposition (plasma CVD). $SiH_4$ is a typical gas containing silicon, and additionally, $Si_2H_6$, $SiH_2Cl_2$, $SiHCl_3$, $SiCl_4$, $SiF_4$, or the like can be used. The gas containing silicon may be diluted with $H_2$ or $H_2$ or and one or more kinds of rare gas elements selected from He, Ar, Kr, and Ne. The dilution ratio is 1:2 to 1:1000, the pressure is approximately 0.1 to 133 Pa, and the power source frequency is 1 to 120 MHz, and preferably 13 to 60 MHz. A substrate heating temperature may be less than or equal to 300° C., preferably, 100 to 250° C. A concentration of an atmospheric constituent impurity such as oxygen, nitrogen, or carbon, as an impurity element in the film, is preferably $1\times10^{20}$ atoms/cm$^3$ or less; in particular, a concentration of oxygen is $5\times10^{19}$ atoms/cm$^3$ or less, preferably $1\times10^{19}$ atoms/cm$^3$ or less. Note that the mobility of a TFT (thin film transistor) using the semiamorphous semiconductor is approximately 1 cm$^2$/Vsec to 10 cm$^2$/Vsec.

As a specific example of a crystalline semiconductor layer, ones made with single crystalline silicon, polycrystalline silicon, silicon germanium, or the like can be cited. They can be formed by laser crystallization, or crystallization by a solid phase epitaxy method using nickel or the like, for example. Single crystal silicon can be used as the semiconductor layer of the transistor 11, by a SmartCut method (registered trademark), for example.

In a case where a semiconductor layer is formed using an amorphous substance, e.g., amorphous silicon, it is preferable that a light-emitting device have circuits including only n-channel transistors as the transistor 11 and the other transistors (transistors included in a circuit for driving a light-emitting element). In the other cases, a light-emitting device may have a circuit including either an n-channel transistor or a p-channel transistor, or may have a circuit including both an n-channel transistor and a p-channel transistor.

Further, the first interlayer insulating films 16a to 16c may be a multilayer as shown in FIGS. 4A, 4C, or a single layer. Note that the first interlayer insulating film 16a is formed using an inorganic material such as silicon oxide or silicon nitride; and the first interlayer insulating film 16b is formed using a self-planarizing substance such as acrylic, siloxane (an organic group in which a skeleton structure is formed of a bond of silicon (Si) and oxygen (O) and at least hydrogen is contained as a substituent), or silicon oxide which can be formed by an application method. In addition, the first interlayer insulating film 16c is formed using a silicon nitride film containing argon (Ar). The substances constituting each of the layers are not particularly limited; therefore, substances other than the substances mentioned here may also be used. Alternatively, a layer made with a substance other than those may be used in combination. As described above, the first interlayer insulating films 16a to 16c may be formed with either an inorganic material or an organic material, or both of them.

The partition layer 18 preferably has a shape in which a curvature radius changes continuously in an edge portion. In addition, the partition layer 18 is formed with acrylic, siloxane, resist, silicon oxide, or the like. Note that the partition layer 18 may be formed with either a film of an inorganic material or a film of an organic material, or both of them.

In FIGS. 4A and 4C, only the first interlayer insulating films 16a to 16c are provided between the transistor 11 and the light-emitting element 12. However, as shown in FIG. 4B, a second interlayer insulating film 19 (19a and 19b) may also be provided in addition to the first interlayer insulating film 16 (16a and 16b). In the light-emitting device shown in FIG. 4B, the first electrode 13 penetrates the second interlayer insulating film 19 and connects to the wiring 17.

The second interlayer insulating film 19 may have a multilayer structure or a single-layer structure like the first interlayer insulating film 16. The second interlayer insulating film 19a is made from acrylic, siloxane (an organic group including a skeleton of a silicon-oxygen bond (Si—O bond) and including at least hydrogen as a substituent), or a self-planarizing substance which can be formed as a film by an application method, such as silicon oxide. The second interlayer insulating film 19b is formed from a silicon nitride film containing argon (Ar). Note that there are no particular limitations on substances forming each layer, and a substance other than the foregoing substances can also be used. A layer made from a substance other than the foregoing materials may be further combined. As described above, the second interlayer insulating film 19 may be formed with either a film of an inorganic material or a film of an organic material, or both of them.

When both the first electrode 13 and the second electrode 14 are formed from light-transmitting substances in the light-emitting element 12, light emission can be extracted through both the first electrode 13 and the second electrode 14 as indicated by the outlined arrows in FIG. 4A. When only the second electrode 14 is formed from a light-transmitting material, light emission can be extracted through only the second electrode 14 as indicated by the outlined arrow in FIG. 4B. In this case, it is preferable to form the first electrode 13 from a highly reflective material or provide a film formed from a highly reflective material (reflective film) below the first electrode 13. When only the first electrode 13 is formed from a light-transmitting material, light emission can be extracted through only the first electrode 13 as indicated by the outlined arrow in FIG. 4C. In this case, it is preferable to form the second electrode 14 from a highly reflective material or provide a reflective film above the second electrode 14.

In the light-emitting element 12, the layer 15 may be stacked so as to operate the light-emitting element 12 when a voltage is applied so that a potential of the second electrode 14 becomes higher than that of the first electrode 13, or the layer 15 may be stacked so as to operate the light-emitting element 12 when a voltage is applied so that a potential of the second electrode 14 becomes lower than that of the first electrode 13. In the former case, the transistor 11 is an n-channel transistor, and in the latter case, the transistor 11 is a p-channel transistor.

As described above, an active matrix light-emitting device in which drive of the light-emitting element is controlled by transistors is explained in Embodiment Mode 6. However, a passive matrix light-emitting device, in which the light-emitting element is driven without providing a particular drive element such as a transistor over the same substrate as the light-emitting element, may also be employed.

The light-emitting device shown in Embodiment Mode 6 has a feature of realizing emission color with high color purity emission colors, since the light-emitting device uses a light-emitting element of the present invention. Further, the light-emitting device also has a feature of various emission colors. Furthermore, the light-emitting device also has a feature of high emission efficiency and low power consumption.

(Embodiment Mode 7)

Because a light-emitting device in which the light-emitting element of the present invention having a sharp emission spectrum is used has excellent color purity and can display images of high quality, by application of the light-emitting device of the present invention to a display portion of an electronic device, an electronic device that displays images of superior quality can be obtained. In addition, the light-emitting device including the light-emitting element of the present invention can be driven with low power consumption because it has excellent emission efficiency. Therefore, electronic devices with low power consumption can be obtained by applying the light-emitting device of the present invention to the display portions of the electronic devices, and for example, a telephone or the like that has long battery standing time, and the like can be obtained. Hereinafter, some examples of electronic devices incorporating a light-emitting device to which a light-emitting element of the present invention is applied are shown.

Figure 5A:
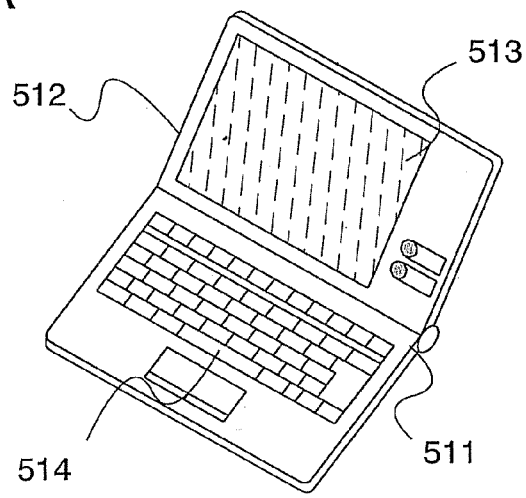
FIGS. 5A to 5C each illustrate an electronic device using a light-emitting device of the present invention.

FIG. 5A is a computer manufactured by applying the present invention, which includes a main body 511, a casing 512, a display portion 513, a keyboard 514, and the like. The computer can be completed by incorporating the light-emitting device including the light-emitting element of the present invention thereinto as a display portion.

Figure 5B:
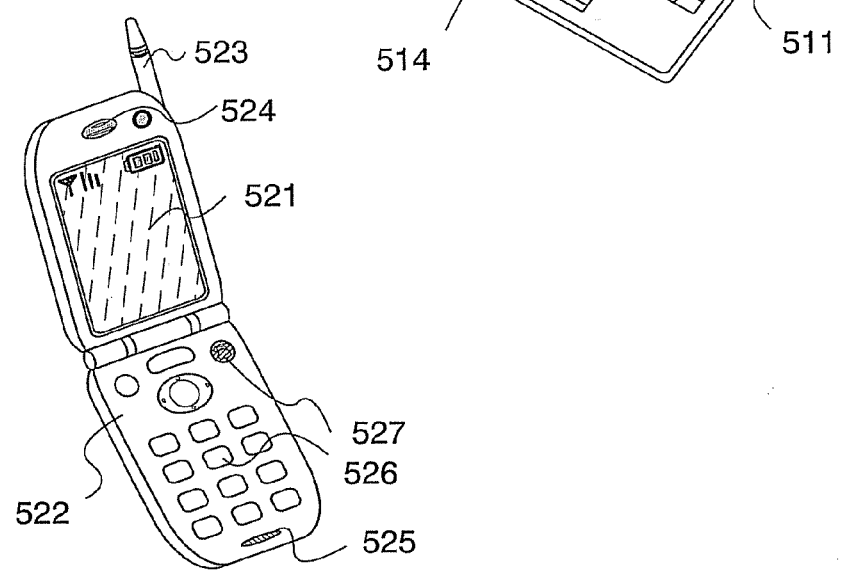

FIG. 5B is a telephone manufactured by applying the present invention, which a main body 522 includes a display portion 521, an audio output portion 524, an audio input portion 525, operation switches 526 and 527, an antenna 523, and the like. The telephone can be completed by incorporating the light-emitting device including the light-emitting element of the present invention in the display portion.

Figure 5C:
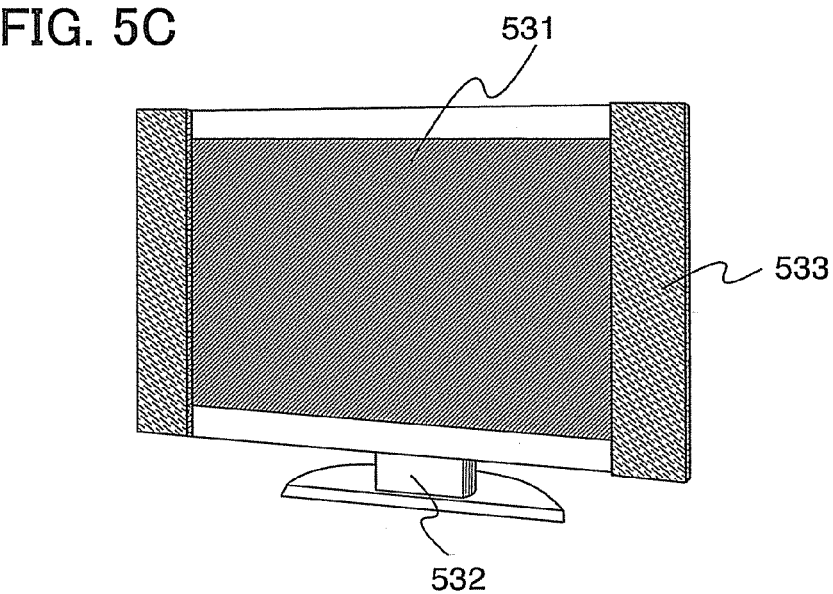

FIG. 5C is a television set manufactured by applying the present invention, which includes a display portion 531, a casing 532, a speaker 533, and the like. The television receiver can be completed by incorporating a light-emitting device having a light-emitting element according to the present invention therein as the display portion.

As the above, the light-emitting device of the present invention is very suitable for a display portion of each of electronic devices.

Although the computer and the like are described in Embodiment Mode 7, besides, the light-emitting device including the light-emitting element of the present invention may also be incorporated in a navigation system, an illumination apparatus, or the like.

In addition, the light-emitting device of the present invention can also be used as an illumination apparatus. One mode using the light-emitting element of the present invention for a lighting device will be described with reference to FIG. 18 to FIG. 20.

Figure 18:
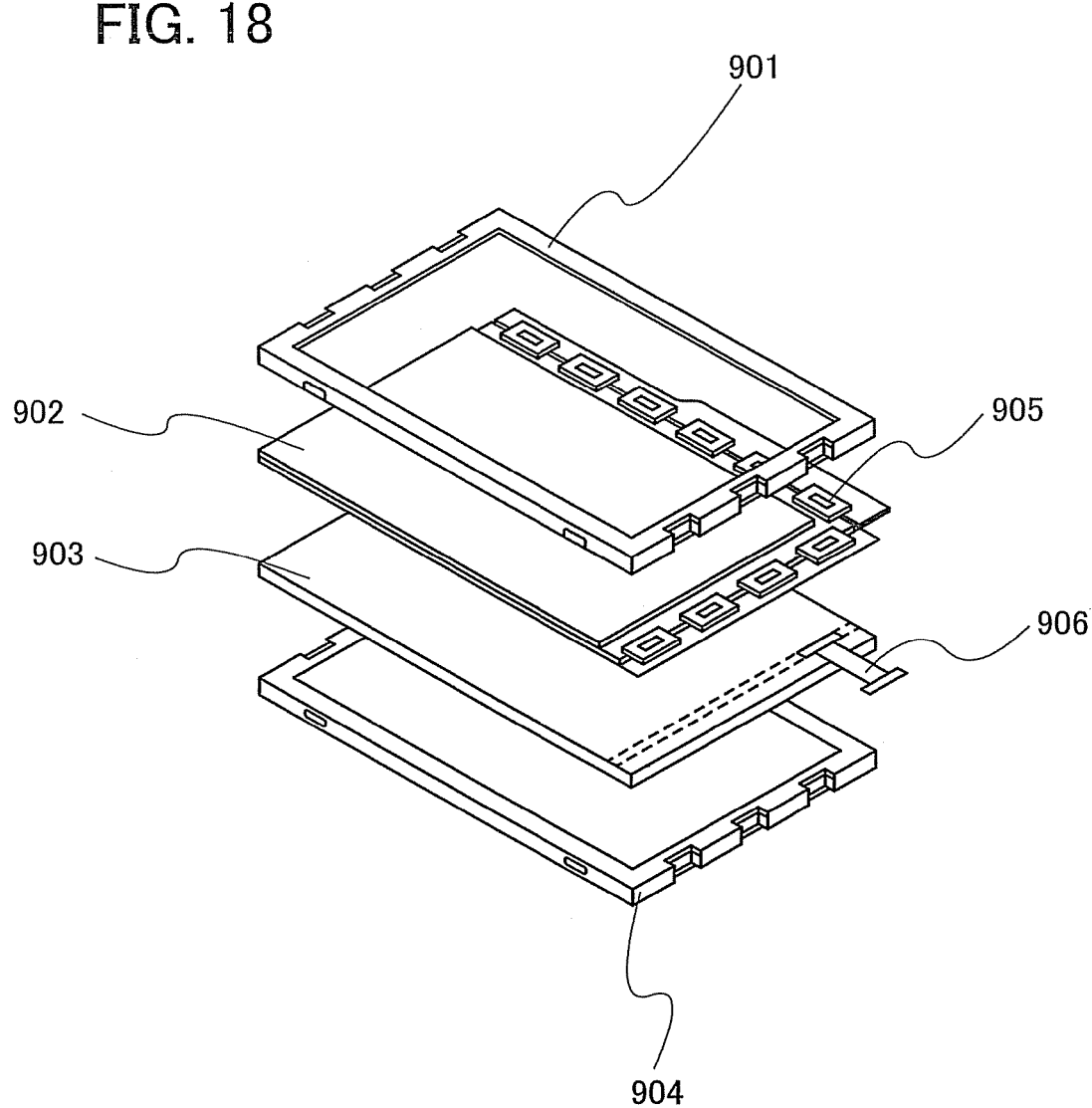
FIG. 18 is a schematic view showing an electronic device according to an aspect of the present invention.

FIG. 18 illustrates an example of a liquid crystal display device in which a light-emitting element including the organometallic complex described in Embodiment Mode 1, i.e., the light-emitting element described in Embodiment Mode 2, is used as a backlight. The liquid crystal display device shown in FIG. 18 includes a chassis 901, a liquid crystal layer 902, a backlight 903, and a chassis 904. The liquid crystal layer 902 is connected to a driver IC 905. The light-emitting element of the present invention is used as the backlight 903, to which current is supplied through a terminal 906.

The backlight 903 for the liquid crystal display device should emit white light or three colors emission of red, green and blue. In the light-emitting element of the present invention, as a method for emitting white light, a plurality of light-emitting layers may be provided as described in Embodiment Mode 3 or Embodiment Mode 4.

In addition, light-emitting elements for red, green and blue are arranged in matrix, and the light-emitting elements are made to emit light at the same time, so that white emission color can be obtained by the whole backlight 903. In this case, the light-emitting element for each color of red, green and blue may be provided to correspond to each pixel for red, green or blue.

Note that the backlight 903 may be formed from one light-emitting element or a plurality of light-emitting elements of the present invention. Alternatively, the backlight 903 may be formed from plural types of light-emitting elements, which emit different colors from the light-emitting element of the present invention.

As described above, a light-emitting element of the present invention can be applied to a backlight of a liquid crystal display device. The area of the backlight can be enlarged, and thus the liquid crystal display device also can be enlarged. Further, a high-quality image can be provided by using a light-emitting element of the present invention with high color purity. Moreover, a backlight with high emission efficiency and reduced power consumption can be provided by using the light-emitting element having high emission efficiency. Moreover, since the backlight using the light-emitting element of the present invention is thin and consumes less electric power, reduction in thickness and power consumption of the liquid crystal display device is possible.

Figure 19:
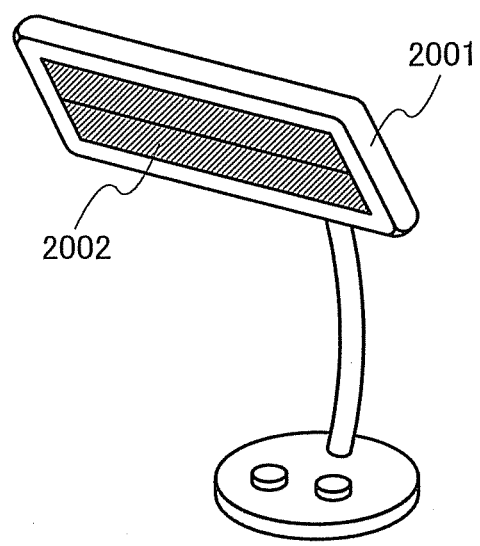
FIG. 19 is a schematic view showing an electronic device according to an aspect of the present invention.

FIG. 19 illustrates an example in which a light-emitting element of the present invention is used for a desk lamp which is an example of illumination apparatuses. The desk lamp shown in FIG. 19 includes a chassis 2001 and a light source 2002, and the light-emitting element of the present invention is used for the light source 2002. The light source 2002 may be formed from one light-emitting element or a plurality of light-emitting elements of the present invention. Alternatively, the light source 2002 may be formed from plural types of light-emitting elements, which emit different colors from the light-emitting element of the present invention. As described above, the light source 2002 can be manufactured by using a light-emitting element of the present invention. In addition, the light source 2002 formed using the light-emitting element having high emission efficiency have high emission efficiency and low power consumption, and thus the desk lamp using the light source also has high emission efficiency and low power consumption.

Figure 20:
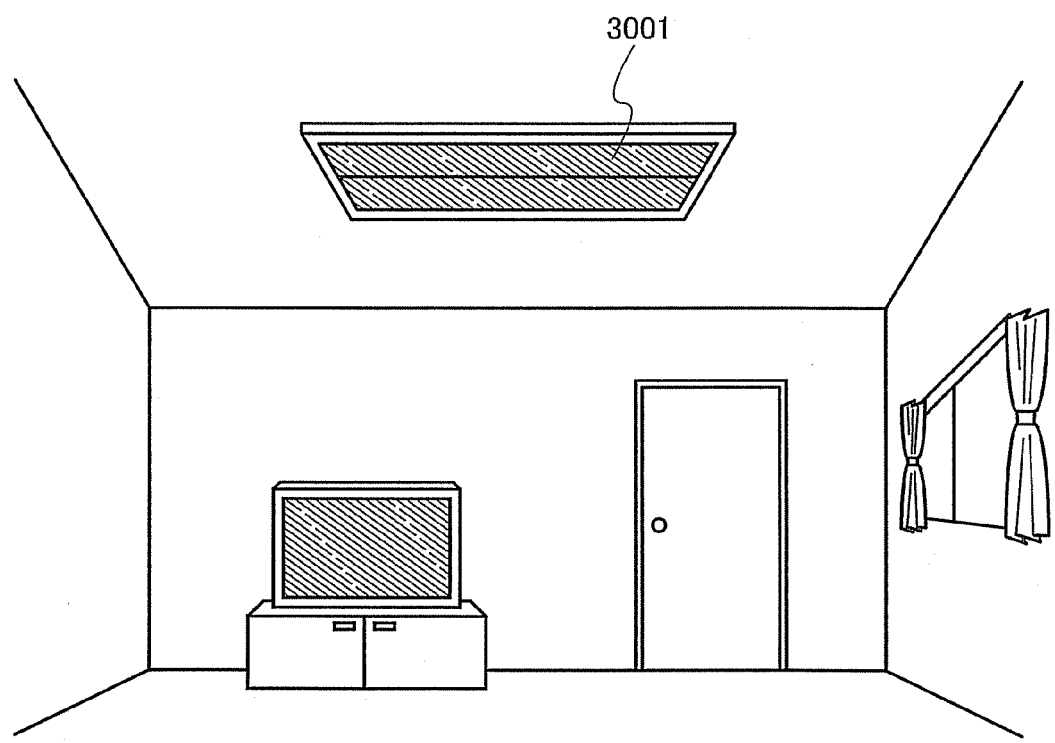
FIG. 20 is a schematic view showing an electronic device according to an aspect of the present invention.

FIG. 20 illustrates an example in which a light-emitting element of the present invention is used for an indoor illumination apparatus 3001. The illumination apparatus 3001 may be formed from one light-emitting element or a plurality of light-emitting elements of the present invention. Alternatively, the illumination apparatus 3001 may be formed from plural types of light-emitting elements, which emit different colors from the light-emitting element of the present invention. As described above, the illumination apparatus 3001 can be manufactured by using a light-emitting element of the present invention. The area of the illumination apparatus 3001 formed using the light-emitting element can be enlarged, and thus it can be used as a large area illumination apparatus. The illumination apparatus 3001 formed using the light-emitting element having high emission efficiency can be an illumination apparatus which is thin and consumes less power.

EXAMPLE 1

Synthesis Example 1

Synthesis Example 1 will specifically describe a synthesis example of an organometallic complex of the present invention represented by the structural formula (1) of Embodiment Mode 1, (acetylacetonato)bis[2-(4-fluorophenyl)-3-methoxy-5-methylpyrazinato]iridium(III) (abbreviation: [Ir(MOFppr-Me)$_2$(acac)]).

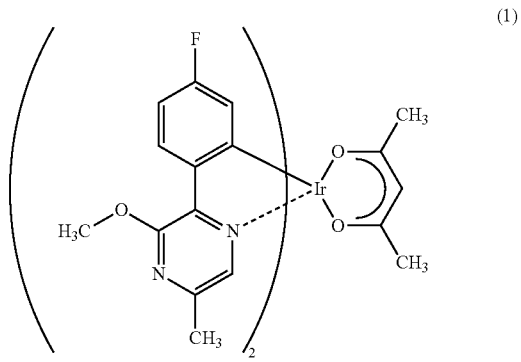

(1)

Step 1: Synthesis of 2-chloro-3-(4-fluorophenyl)pyrazine

First, 5.06 g of 2,3-dichloropyrazine, 5.23 g of 4-fluorophenyl boronic acid, 22.16 g of cesium carbonate, and 200 mL of dioxane were put in a three-neck flask equipped with a reflux pipe, and 0.467 g of tris(dibenzylideneacetone)dipalladium(0) (abbreviation: Pd$_2$(dba)$_3$) and 2.5 mL of tricyclohexylphosphine (abbreviation: Cy$_3$P) were added thereto while the mixture was stirred under a nitrogen atmosphere, and they were reacted at 85° C. for 11 hours. After the reaction, the reaction solution was cooled down to room temperature and filtrated. A solvent of the obtained filtrate was distilled off, and the obtained residue was refined with a column chromatography using dichloromethane as a development solvent, so that 2-chloro-3-(4-fluorophenyl)pyrazine was obtained (light yellow powder, yield: 55%). A synthesis scheme of Step 1 is shown by the following (a1-1).

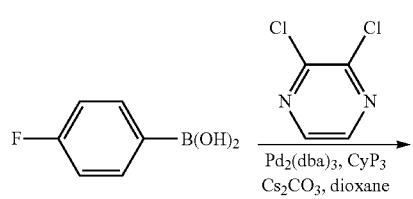

(a1-1)

Step: 2 Synthesis of 2-(4-fluorophenyl)-3-methoxypyrazine

Next, 3.87 g of 2-chloro-3-(4-fluorophenyl)pyrazine, 2.01 g of sodium methoxide, and 30 mL of methanol were put in a three-neck flask equipped with a reflux pipe, and reacted by being heated and refluxed under a nitrogen atmosphere for three hours. After the reaction, the reaction solution was cooled down to room temperature, water was added thereto, and an organic layer was extracted with dichloromethane. The obtained organic layer was washed with a saturated saline and water, and dried with magnesium sulfate. Then, magnesium sulfate was removed by filtration and the solvent was distilled off, so that 2-(4-fluorophenyl)-3-methoxypyrazine was obtained (milky white powder, yield: 96%). A synthetic scheme of Step 2 is shown in the following (a1-2).

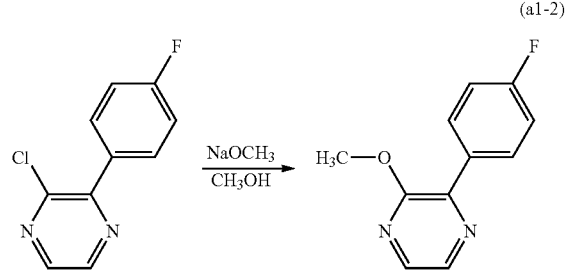

(a1-2)

Step 3: 2-(4-fluorophenyl)-3-methoxy-5-methylpyrazine (abbreviation: HMOFppr-Me)

Further, 3.24 g of 2-(4-fluorophenyl)-3-methoxypyrazine and 80 mL of diethyleter were put in a three-neck flask, and 20 mL of a diethylether solution of methyllithium (1.20 mol/L) was dropped while the mixture was stirred under a nitrogen atmosphere, and stirred to be reacted for one week. After the reaction, water was added to the reaction solution, and an organic layer was extracted with dichloromethane. The obtained organic layer was washed with water, and dried with magnesium sulfate. Magnesium sulfate was removed by filtration and the solvent was distilled off. The obtained residue was refined with a column chromatography using dichloromethane as a development solvent, so that an objective pyrazine derivative, HMOFppy-Me (milky white powder, yield: 15%). A synthesis scheme of Step 3 is shown by the following (a1-3).

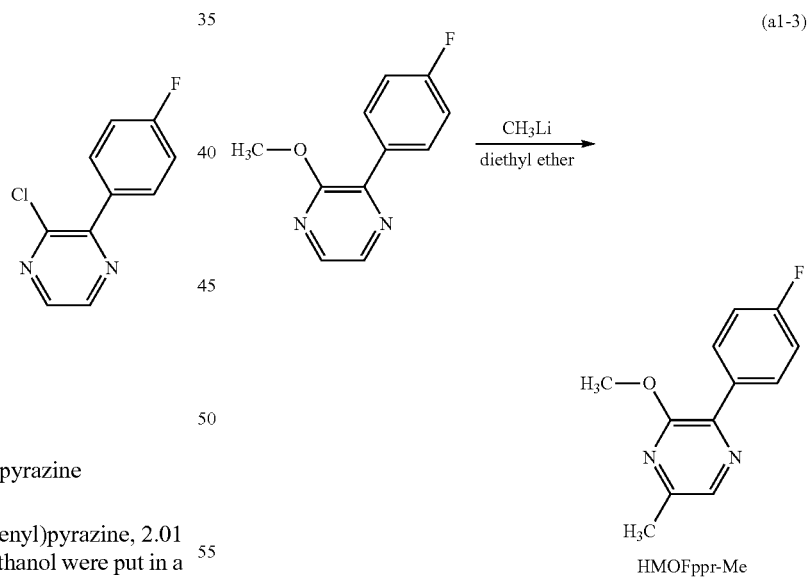

(a1-3)

Step 4: Synthesis of di-μ-chloro-bis{bis[2-(4-fluorophenyl)-3-methoxy-5-methylpyrazinato]iridium (III)}(abbreviation: [Ir(MOFppr-Me)$_2$Cl]$_2$)

Next, 24 mL of 2-ethoxyethanol, 8 mL of water, 0.52 g of the pyrazine derivative HMOFppy-Me obtained in Step 3, and 0.36 g of iridium chloride hydrate (IrCl$_3$.H$_2$O) (manufactured by Sigma-Aldrich Corp.) were put in an egg plant flask equipped with a reflux pipe, and the inside thereof was substituted by argon. Then, the reaction container was subjected to irradiation of a microwave (2.45 GHz, 150 W) for one hour to be heated and reacted. Orange powder precipitated from the reaction solution was filtrated and washed with ethanol, so that a binuclear complex, [Ir(MOFppr-Me)$_2$Cl]$_2$ was obtained (yield: 45%). A synthesis scheme of Step 4 is shown by the following (b1).

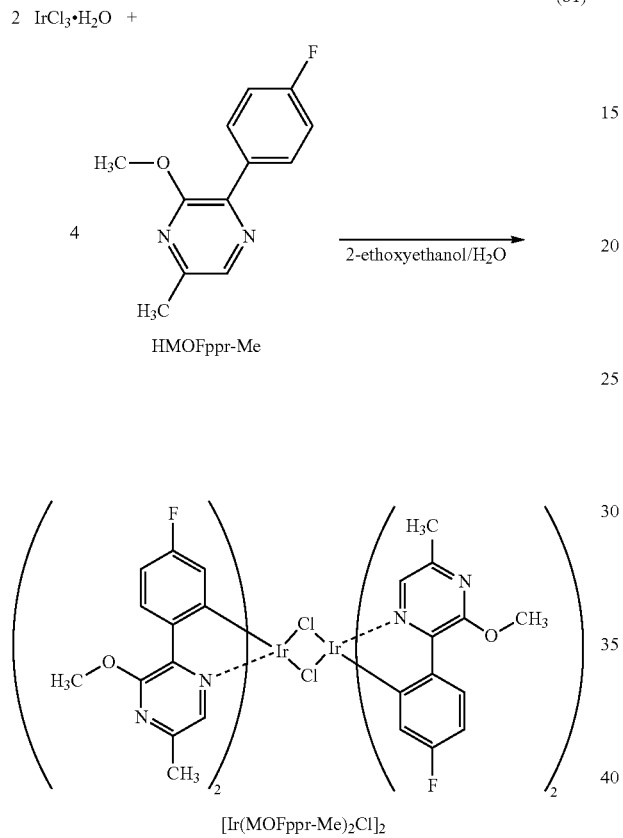

Step 5: Synthesis of (acetylacetonato)bis[2-(4-fluorophenyl)-3-methoxy-5-methylpyradinato]iridium (III) (abbreviation: [Ir(MOFppr-Me)$_2$(acac)]

Further, 30 mL of 2-ethoxyethanol, 0.36 g of the binuclear complex [Ir(MOFppr-Me)$_2$Cl]$_2$ obtained in Step 4, 0.083 mL of acetylacetone, 0.29 g of sodium carbonate were put in an egg plant flask equipped with a reflux pipe, and the inside thereof was substituted by argon. Then, this reaction container was subjected to irradiation of a microwave (2.45 GHz, 150 W) for 30 minutes to be heated and reacted. The reaction solution was cooled down to room temperature, filtrated, and the solvent wad distilled off. The obtained residue was recrystallized with dichloromethane-methanol, so that an organometallic complex of the present invention, [Ir(MOFppr-Me)$_2$(acac)] was obtained (orange micro crystal, yield: 33%). A synthesis scheme of Step 5 is shown by the following (c1).

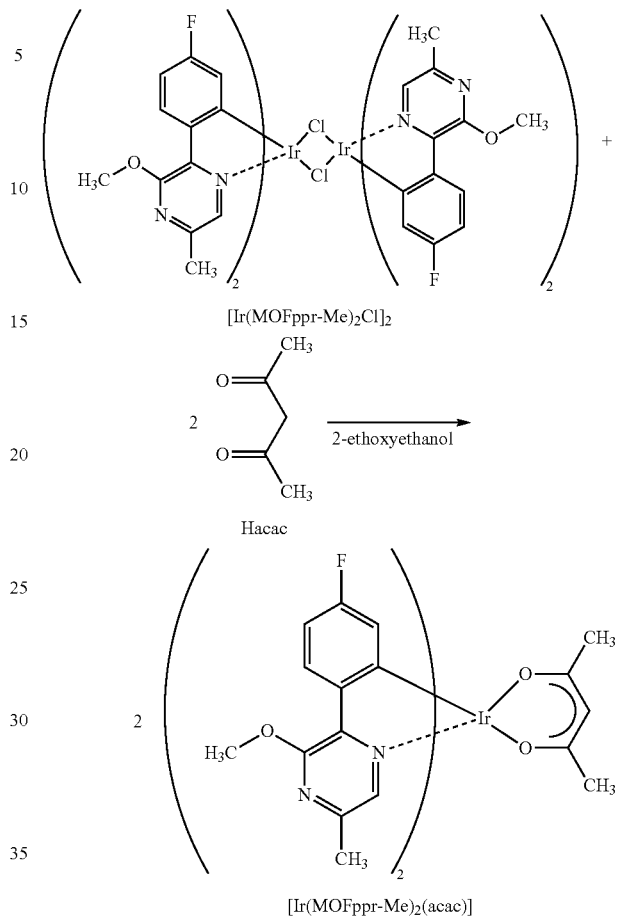

Figure 6:
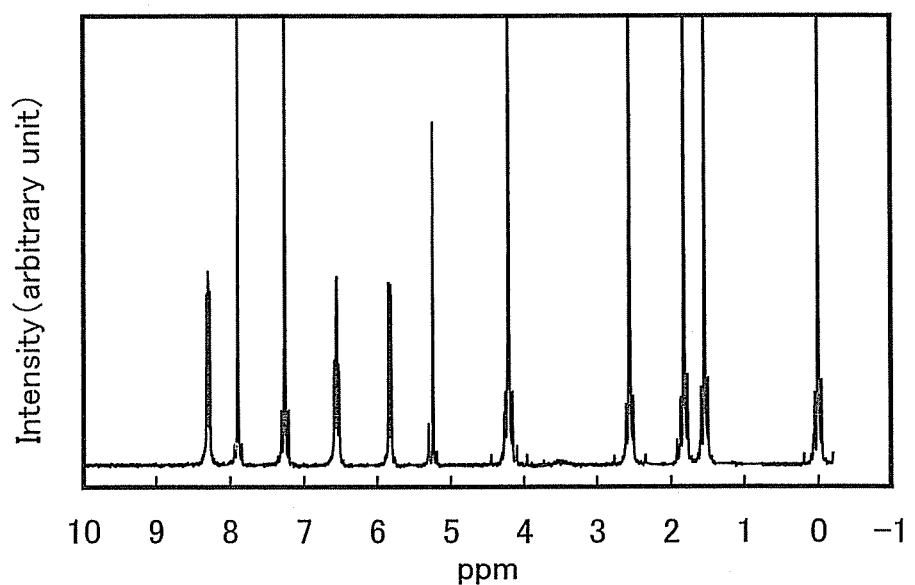
FIG. 6 is a $^1$H-NMR chart of an organometallic complex, [Ir(MOFppr-Me)$_2$(acac)], according to an aspect of the present invention.

An analysis result by nuclear magnetic resonance spectrometry ($^1$H-NMR) of the orange micro crystal obtained in Step 5 is shown below. FIG. 6 is a $^1$H-NMR chart thereof. According to FIG. 6, it is found that the organometallic complex of the present invention [Ir(MOFppr-Me)$_2$(acac)] represented by the above structural formula (1) was obtained in Synthesis Example 1.

$^1$H-NMR. δ (CDCl$_3$): 1.82 (s, 6H), 2.56 (s, 6H), 4.21 (s, 6H), 5.24 (s, 1H), 5.82 (d, 2H), 6.56 (t, 2H), 7.89 (s, 2H), 8.30 (m, 2H).

Figure 7:
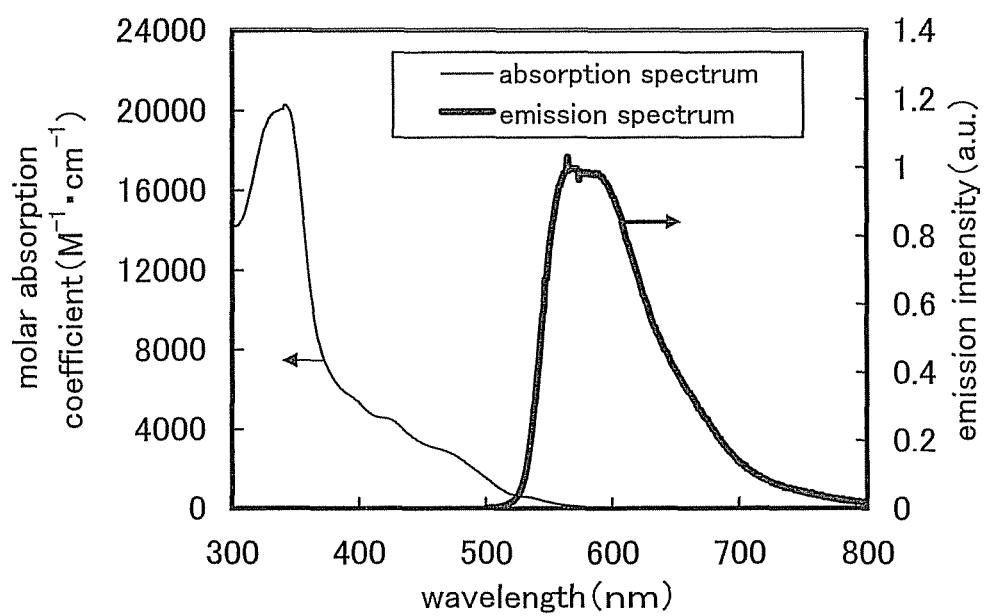
FIG. 7 is a graph showing an ultraviolet-visible absorption spectrum and an emission spectrum of the organometallic complex [Ir(MOFppr-Me)$_2$(acac)], according to an aspect of the present invention.

An absorption spectrum and an emission spectrum (excitation wavelength: 468 nm) of [Ir(MOFppr-Me)$_2$(acac)] were measured. The absorption spectrum was measured by using a degassed dichloromethane solution (0.14 mmol/L) at room temperature by using an ultraviolet-visible spectrophotometer (V-550, by JASCO Corporation). The emission spectrum was measured by using a degassed dichloromethane solution (0.48 mmol/L) at room temperature by using a spectrofluorometer (FS920, by Hamamatsu Photonics K. K.) The measurement results are shown in FIG. 7. The horizontal axis indicates a wavelength and the vertical axis indicates a molar absorption coefficient and an emission intensity.

The peak of the emission spectrum lies at 570 nm, and orange emission was observed.

It is observed that the organometallic complex [Ir(MOFppr-Me)$_2$(acac)] of the present invention has several absorption peaks in the visible light region. This absorption is unique to some organometallic complexes such as an ortho-metalated complex, and is considered to correspond to singlet MLCT transition, triplet π-π* transition, triplet MLCT transition, or the like. In particular, the longest wavelength absorption peak extends over a broad range in the visible light region. Thus, this absorption peak is considered to correspond to the triplet MLCT transition. In other words, it is considered that the organometallic complex [Ir(MOFppr-Me)$_2$(acac)] of the present invention is a compound capable of direct photoexcitation or intersystem crossing to a triplet excited state. Therefore, it can be considered that obtained emission is light emission from the triplet excited state, that is, phosphorescence.

EXAMPLE 2

Example 2 will specifically describe a light-emitting element using the organometallic complex of the present invention, [Ir(MOFppr-Me)$_2$(acac)] synthesized in Synthesis Example 1 of Example 1, as a light-emitting substance. FIG. 1 illustrates a structure of the light-emitting element.

First, a glass substrate, over which indium tin oxide containing silicon oxide (ITSO) was formed with a thickness of 110 nm, was prepared. The periphery of the ITSO surface was covered with an insulating film so that a surface of ITSO of 2 mm×2 mm was exposed. ITSO was formed as a first electrode 101 serving as an anode of the light-emitting element. As a pretreatment for forming the light-emitting element over the substrate, the surface of the substrate was washed with a porous resin brush, and baked at 200° C. for one hour, then, a UV ozone treatment was conducted for 370 seconds.

Subsequently, the substrate was fixed to a holder provided in a vacuum evaporation apparatus so that the surface provided with ITSO faced downward.

After pressure in the vacuum evaporation apparatus was reduced to $10^{-4}$ Pa, NPB represented by the following structural formula (i) and molybdenum(VI) oxide were co-deposited so as to meet NPB:molybdenum(VI) oxide=4:1 (mass ratio), whereby a hole-injecting layer 111 was formed. The hole-injecting layer 111 was 50 nm thick. Note that a co-evaporation method is an evaporation method in which a plurality of different substances is concurrently vaporized from respective different evaporation sources. Next, NPB was deposited to be 10 nm thick, whereby a hole-transporting layer 112 was formed. Further, over the hole-transporting layer 112, 4-(9H-carbazol-9-yl)-4'-(5-phenyl-1,3,4-oxadiazol-2-yl)triphenylamine (abbreviation: YGAO11) and [Ir(MOFppr-Me)$_2$(acac)] synthesized in Synthesis Example 1 were co-evaporated such that the mass ratio of YGAO11 to [Ir(MOFppr-Me)$_2$(acac)] was 1:0.05 (YGAO11: [Ir(MOFppr-Me)$_2$(acac)]=1:0.05), and thereby a light-emitting layer 113 was formed. The film thickness was 30 nm. Then, BAlq represented by the following structural formula (iii) was deposited to be 10 nm thick, whereby an electron-transporting layer 114 was formed. Further, over the electron-transporting layer 114, Alq$_3$ represented by the following structural formula (Iv) and lithium (Li) were co-deposited so as to meet Alq$_3$:Li=1:0.01 (mass ratio), whereby an electron-injecting layer 115 was formed. The film thickness was 40 nm. Finally, aluminum was formed to be 200 nm thick as a second electrode 102 which functions as a cathode, whereby a light-emitting element of the present invention was obtained. It is to be noted that, in all of the above evaporation processes, evaporation was performed by a resistance heating method.

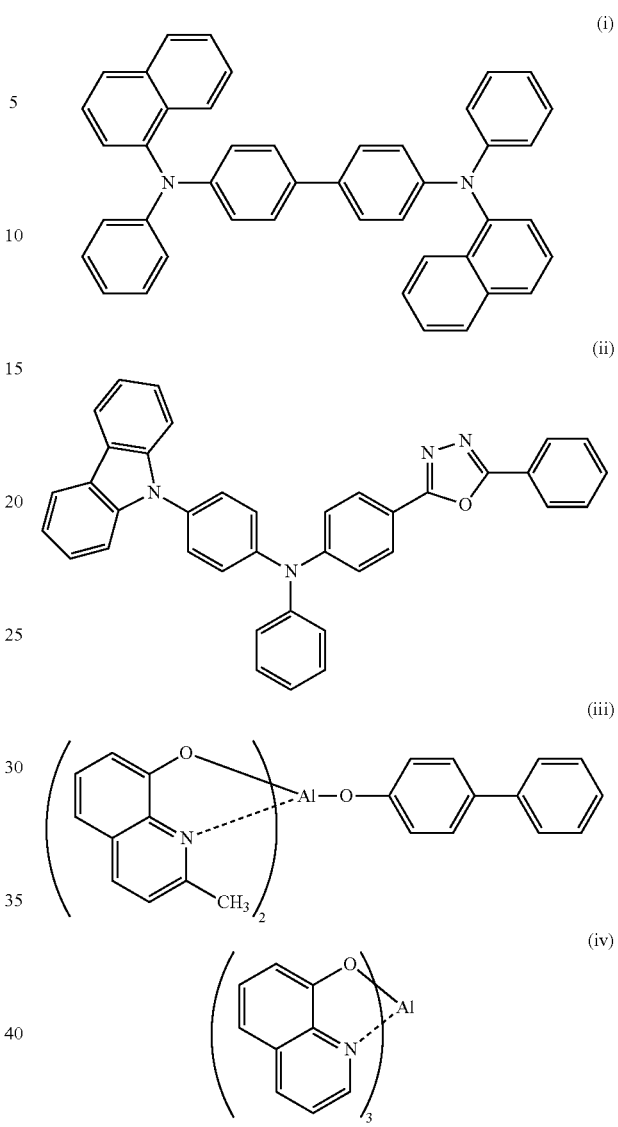

After sealing this light-emitting element in a glove box with a nitrogen atmosphere so as not to expose the light-emitting element to air, operation characteristics of the light-emitting element were measured. Note that the measurements were performed at room temperature (an atmosphere kept at 25° C.).

Figure 8:
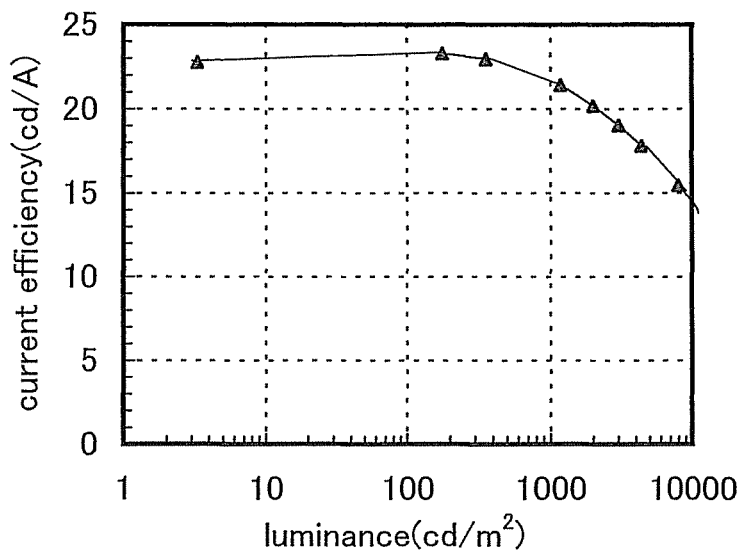
FIG. 8 is a graph showing an emission efficiency of a light-emitting element using the organometallic complex [Ir(MOFppr-Me)$_2$(acac)], according to an aspect of the present invention.
Figure 9:
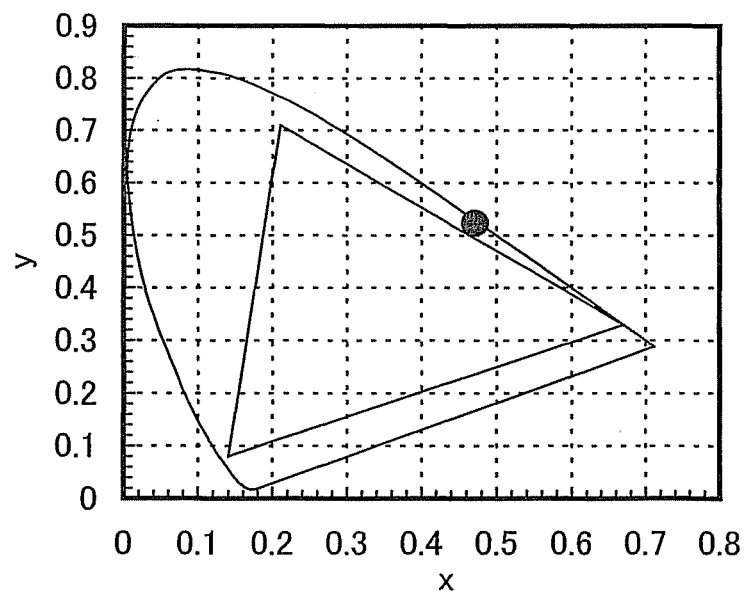
FIG. 9 is a graph showing an NTSC chromaticity coordinate of the light-emitting element using the organometallic complex [Ir(MOFppr-Me)$_2$(acac)], according to an aspect of the present invention.

FIG. 8 shows luminance-current efficiency characteristics of the light-emitting element. This light-emitting element emits light at a luminance of 1170 cd/m$^2$ by allowing current flow with a current density of 5.46 mA/cm$^2$. At this time, the current efficiency was 21.4 cd/A and thus the light-emitting element exhibited a high emission efficiency. When the current efficiency was converted to an external quantum efficiency, the external quantum efficiency was 6.31%. In addition, FIG. 9 shows CIE chromaticity coordinates at this time and the CIE chromaticity coordinates were (x, y)=(0.47, 0.52). Thus, yellow orange light emission was obtained. As shown in FIG. 9, the CIE chromaticity coordinates of the light-emitting element of this example exist outside the color reproduction region of NTSC standard (which is the inside of the triangle in FIG. 10), and thus it is known that the light-emitting element exhibits high color purity.

Figure 10:
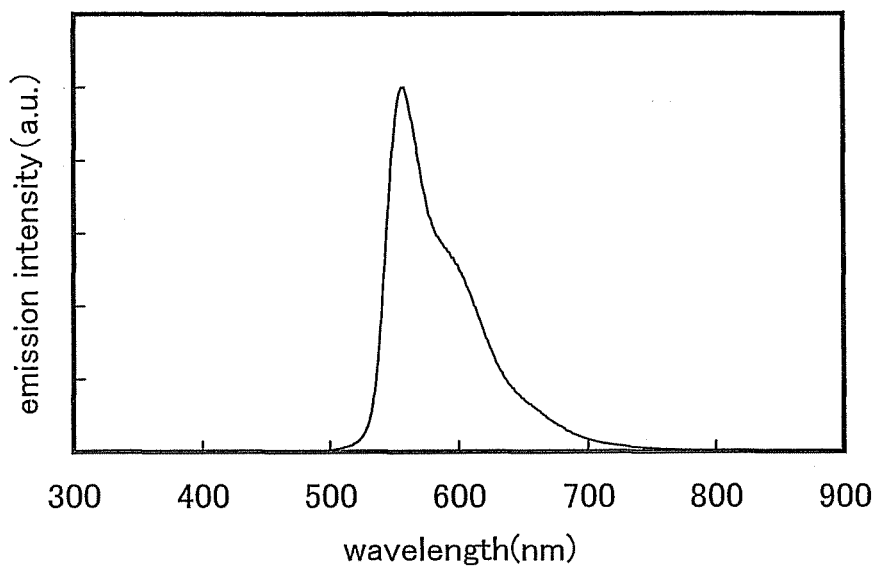
FIG. 10 is a graph showing an emission spectrum of the light-emitting element using the organometallic complex [Ir(MOFppr-Me)$_2$(acac)], according to an aspect of the present invention.
Figure 11:
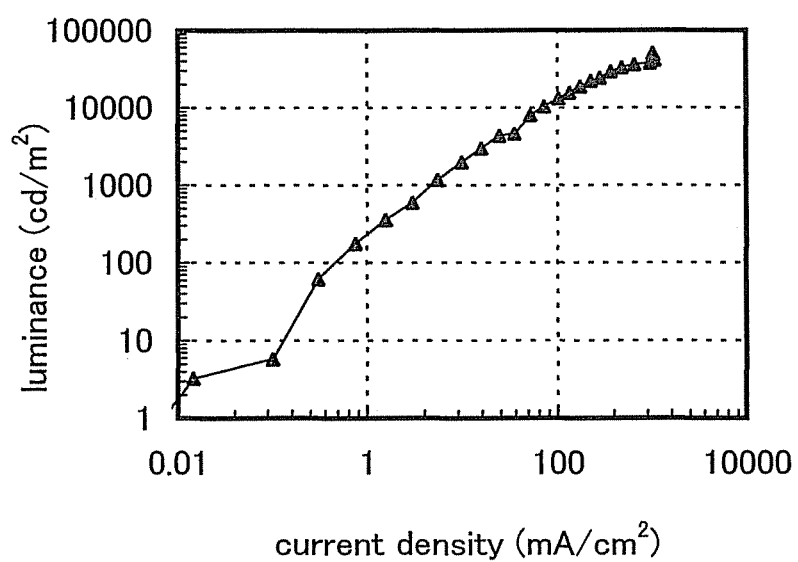
FIG. 11 is a graph showing current density-luminance characteristics of the light-emitting element using the organometallic complex [Ir(MOFppr-Me)$_2$(acac)], according to an aspect of the present invention.
Figure 12:
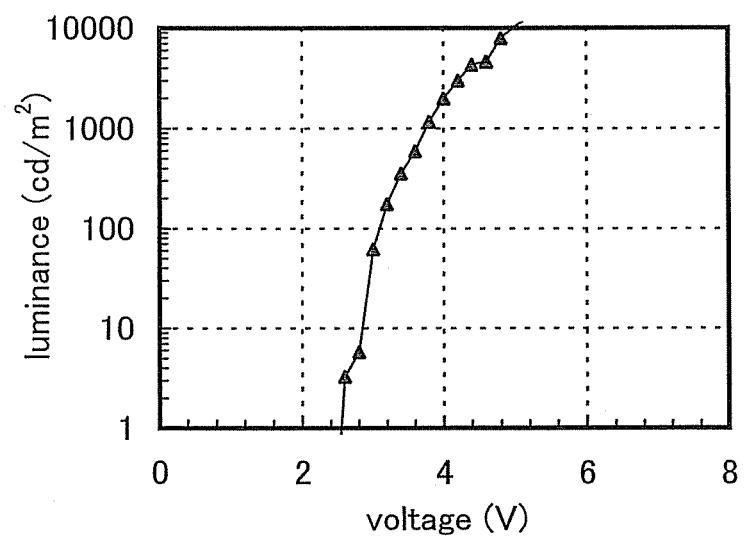
FIG. 12 is a graph showing voltage-luminance characteristics of the light-emitting element using the organometallic complex [Ir(MOFppr-Me)$_2$(acac)], according to an aspect of the present invention.
Figure 13:
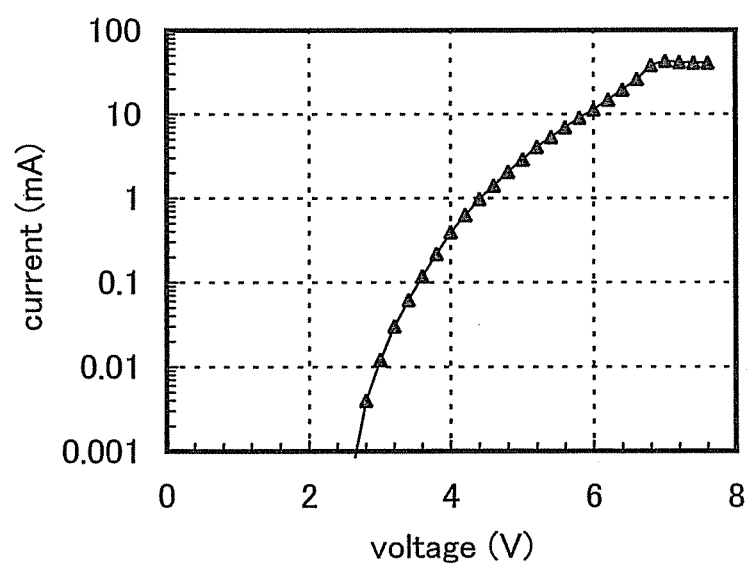
FIG. 13 is a graph showing voltage-current characteristics of the light-emitting element using the organometallic complex [Ir(MOFppr-Me)$_2$(acac)], according to an aspect of the present invention.
Figure 14:
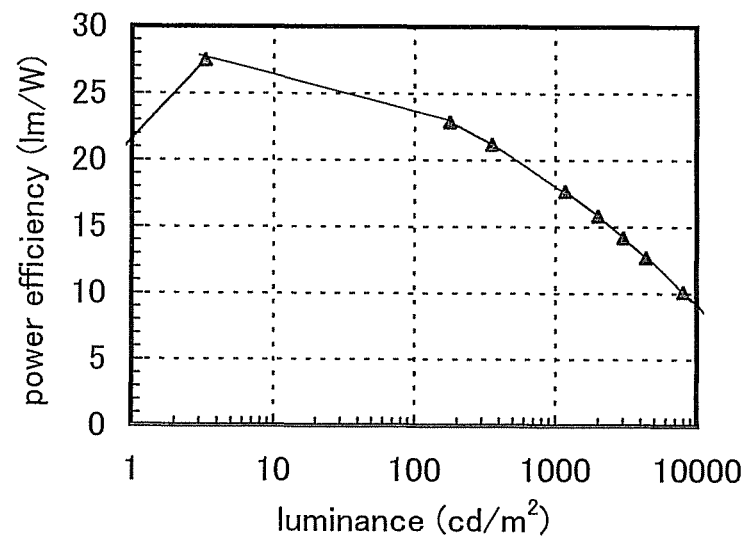
FIG. 14 is a graph showing luminance-power efficiency characteristics of the light-emitting element using the organometallic complex [Ir(MOFppr-Me)$_2$(acac)], according to an aspect of the present invention.
Figure 15:
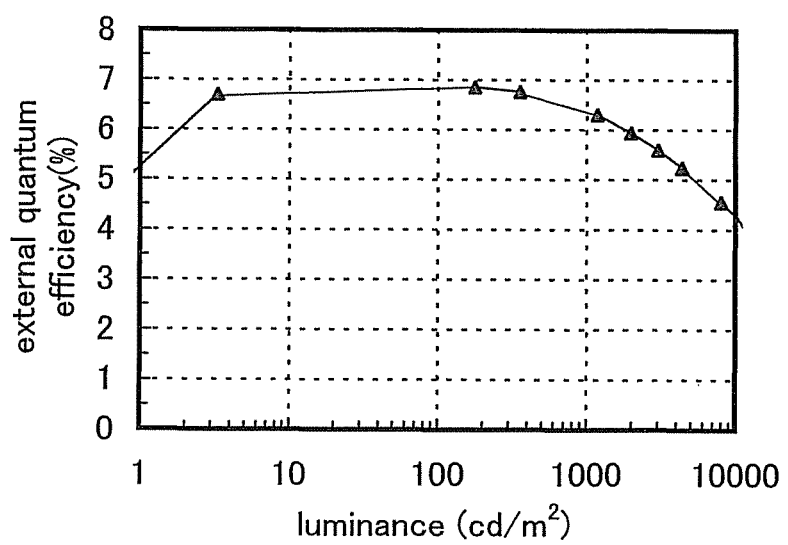
FIG. 15 is a graph showing luminance-external quantum efficiency characteristics of the light-emitting element using the organometallic complex [Ir(MOFppr-Me)$_2$(acac)], according to an aspect of the present invention.

FIG. 10 shows an emission spectrum when a current at a current density of 0.5 mA/cm² was supplied to this light-emitting element. As shown in FIG. 10, the emission spectrum has a peak at 558 nm, and it indicates that the peak results from light emission of [Ir(MOFppr-Me)₂(acac)] which is an organometallic complex of the present invention. Full width at half-maximum of the emission spectrum was 58 nm and the spectrum was sharp.

FIG. 11, FIG. 12, FIG. 13, FIG. 14 and FIG. 15 show current density-luminance characteristics, voltage-luminance characteristics, voltage-current characteristics, luminance-power efficiency characteristics, and luminance-external quantum efficiency characteristics of the fabricated light-emitting element, respectively.

EXAMPLE 3

Synthesis Example 2

Synthesis example 2 will specifically describe a synthesis example of an organometallic complex of the present invention represented by the structural formula (12) of Embodiment Mode 1, (acetylacetonato)bis(2-phenyl-3-methoxy-5-methylpyrazinato)iridium(III) (abbreviation: [Ir(MOppr-Me)₂(acac)]).

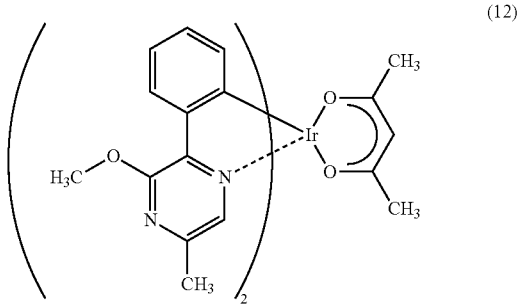

(12)

Step 1: Synthesis of 2-phenyl-3-methoxypyrazine

First, in a three-neck flask, 11.30 g of 2-methoxypyrazine and 200 mL of diethylether were put, and a dibutyl ether solution (2.1 mol/L) of phenyl lithium was dropped thereto while the mixture was cooled down with ices and stirred under a nitrogen atmosphere, and stirred to be reacted for 20 hours. After the reaction, water was added to the reaction solution, and an organic layer was extracted with ethyl acetate. The obtained organic layer was washed with water, and dried with magnesium sulfate. Magnesium sulfate was removed by filtration and the solvent was distilled off. The obtained residue was refined with a column chromatography using dichloromethane as a development solvent, so that 2-phenyl-3-methoxypyrazine was obtained (light yellow powder, yield: 12%). A synthesis scheme of Step 1 is shown by the following (a2-1).

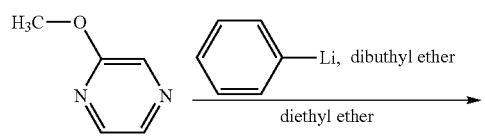

(a2-1)

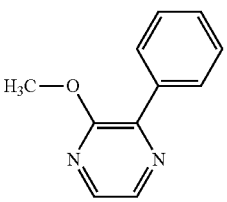

Step 2: Synthesis of 2-phenyl-3-methoxy-5-methylpyrazine (abbreviation: HMOppr-Me)

First, 2.16 g of 2-phenyl-3-methoxypyrazine obtained in the above Step 1 and 30 mL of diethylether were put in a three-neck flask, and 14.5 mL of a diethylether solution (1.20 mol/L) of methyllithium was dropped thereto while the mixture was stirred under a nitrogen atmosphere, and then stirred to be reacted for 20 hours. After the reaction, water was added to the reaction solution, and an organic layer was extracted with dichloromethane. The obtained organic layer was washed with water, and dried with magnesium sulfate. Magnesium sulfate was removed by filtration and the solvent was distilled off. The obtained residue was refined with a column chromatography using dichloromethane as a development solvent, so that an objective alkoxypyrazine derivative, HMOppe-Me, was obtained (milky white powder, yield: 20%). A synthesis scheme of Step 2 is shown by the following (a2-2).

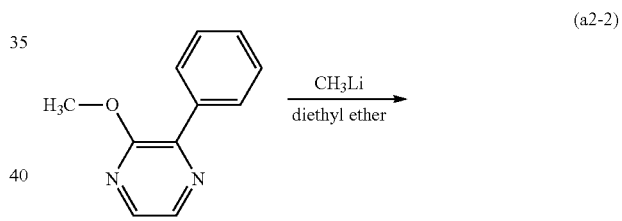

(a2-2)

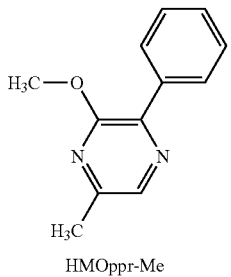

HMOppr-Me

Step 3: Synthesis of di-μ-chloro-bis[bis(2-phenyl-3-methoxy-5-methylpyrazinato]iridium(III)} (abbreviation: [Ir(MOppr-ME)₂Cl]₂)

Next, 15 mL of 2-ethoxyethanol, 5 mL of water, 0.47 g of the pyrazine derivative HMOppr-Me obtained in Step 2 described above, and 0.35 g of iridium chloride hydrate (IrCl₃.H₂O) (manufactured by Sigma-Aldrich Corp.) were put in an egg plant flask with a reflux pipe attached, and the inside thereof was substituted by argon. Then, the reaction container was subjected to irradiation of a microwave (2.45 GHz, 120 W) for 30 minutes to be heated and reacted. Red powder precipitated from the reaction solution was filtrated and washed with ethanol, so that a binuclear complex, [Ir(MOppr-Me)$_2$Cl]$_2$ was obtained (yield: 33%). A synthesis scheme of Step 3 is shown by the following (c2).

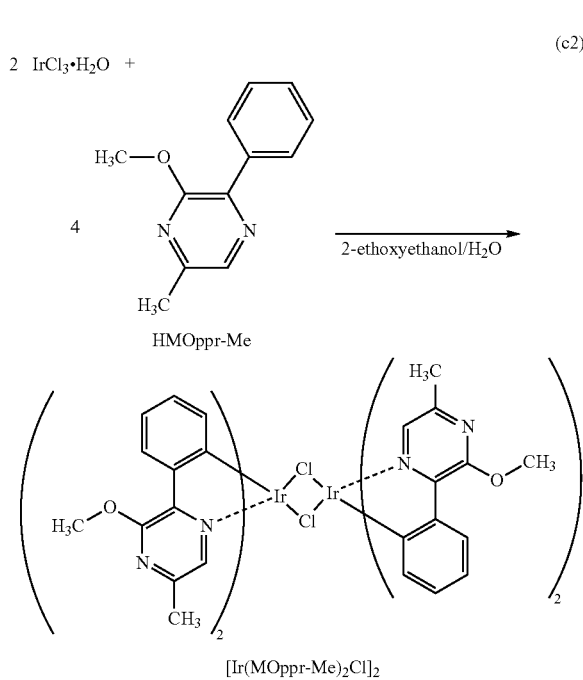

(c2)

[Ir(MOppr-Me)$_2$Cl]$_2$

Step 4: Synthesis of (acethylacetonato)bis(2-phenyl-3-methoxy-5-methylpyrazinato)iridium(III)] (abbreviation: [Ir(MOppr-Me)$_2$(acac)])

Further, 10 mL of 2-ethoxyethanol, 0.25 g of the binuclear complex [Ir(MOppr-Me)$_2$Cl]$_2$ obtained in Step 3 described above, 0.06 mL of acethylacetone, and 0.21 g of sodium carbonate were put in an egg plant flask with a reflux pipe attached, and the inside thereof was substituted by argon. Then, the reaction container was subjected to irradiation of a microwave (2.45 GHz, 100 W) for 30 minutes to be heated and reacted. The reaction solution was cooled down to room temperature, filtrated, and the solvent was distilled off. The obtained residue was refined with a column chromatography using dichloromethane as a development solvent, so that an organometallic complex of the present invention, [Ir(MOppr-Me)$_2$(acac)] was obtained (orange powder, yield: 10%). A synthesis scheme of Step 4 is shown by the following (d2).

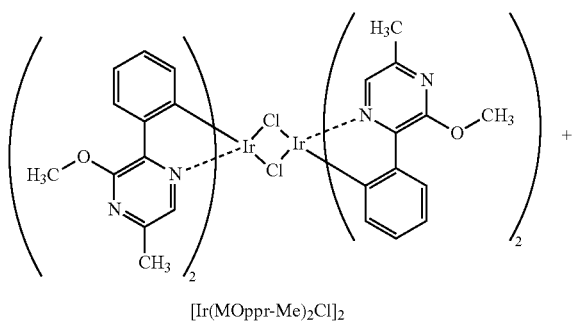

(d2)

[Ir(MOppr-Me)$_2$Cl]$_2$

+

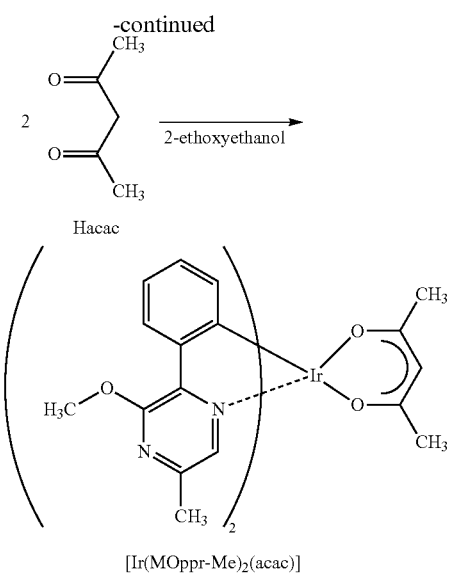

[Ir(MOppr-Me)$_2$(acac)]

Figure 16:
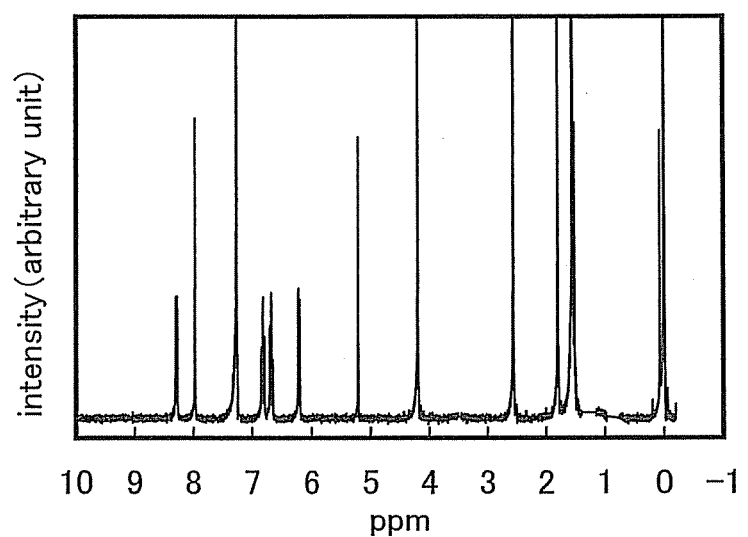
FIG. 16 is a $^1$H-NMR chart of an organometallic complex, [Ir(MOppr-Me)$_2$(acac)], according to an aspect of the present invention.

An analysis result by nuclear magnetic resonance spectrometry ($^1$H-NMR) of the orange powder obtained in Step 4 is described below. FIG. 16 is a $^1$H-NMR chart thereof. Thus, it is found from FIG. 16 that the organometallic complex of the present invention [Ir(MOppr-Me)$_2$(acac)] represented by the above structural formula (12) was obtained in Synthetic Example 1.

$^1$H-NMR. δ (CDCl$_3$): 1.80 (s, 6H), 2.56 (s, 6H), 4.20 (s, 6H), 5.21 (s, 1H), 6.22 (dd, 2H), 6.68 (dt, 2H), 6.82 (dt, 2H), 7.98 (s, 2H), 8.29 (dd, 2H).

Figure 17:
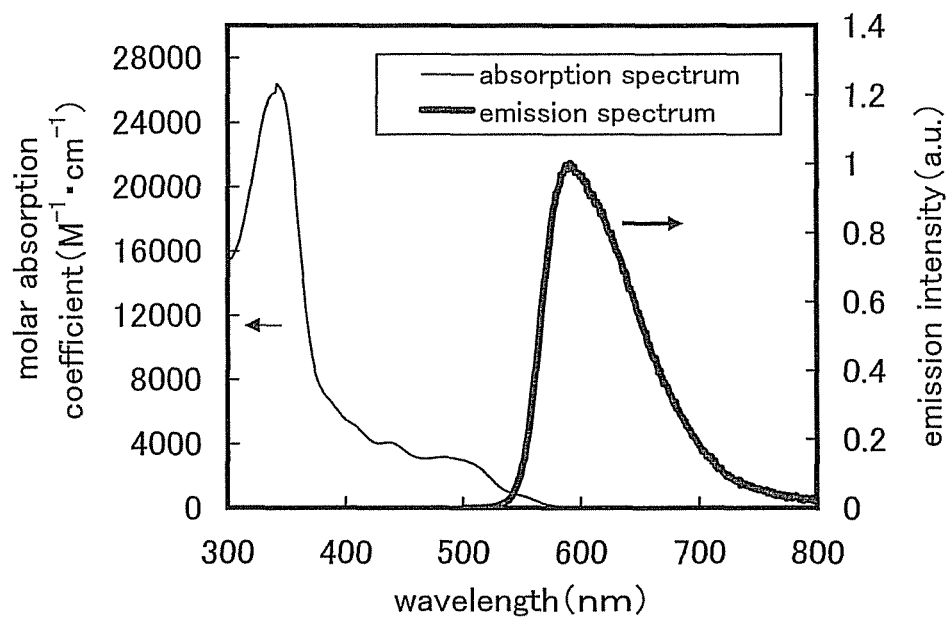
FIG. 17 is a graph showing an ultraviolet-visible absorption spectrum and an emission spectrum of the organometallic complex [Ir(MOppr-Me)$_2$(acac)], according to an aspect of the present invention.

An absorption spectrum and an emission spectrum (excitation wavelength: 468 nm) of [Ir(MOppr-Me)$_2$(acac)] were measured. The absorption spectrum was measured by using a degassed dichloromethane solution (0.12 mmol/L) at room temperature by using an ultraviolet-visible spectrophotometer (V-550, by JASCO Corporation). The emission spectrum was measured by using a degassed dichloromethane solution (0.42 mmol/L) at room temperature by using a spectrofluorometer (FS920, by Hamamatsu Photonics K. K.) The measurement results are shown in FIG. 17. The horizontal axis indicates a wavelength and the vertical axis indicates a molar absorption coefficient and an emission intensity.

The peak of the emission spectrum lies at 592 nm, and orange emission was observed.

It is observed that the organometallic complex [Ir(MOppr-Me)$_2$(acac)] has several absorption peaks in the visible light region. This absorption is unique to some organometallic complexes such as an ortho-metalated complex, and is considered to correspond to singlet MLCT transition, triplet π-π* transition, triplet MLCT transition, or the like. In particular, the longest wavelength absorption peak extends over a broad range in the visible light region. Thus, this absorption is considered to correspond to the triplet MLCT transition. In other words, it is considered that the organometallic complex [Ir(MOppr-Me)$_2$(acac)] is a compound capable of direct photo-excitation or intersystem crossing to a triplet excited state. Therefore, it can be considered that obtained emission is light emission from the triplet excited state, that is, phosphorescence.

This application is based on Japanese Patent Application Serial No. 2007-148458 filed with Japan Patent Office on Jun. 4, 2007, the entire contents of which are hereby incorporated by reference.

The invention claimed is:

1. An organometallic complex represented by a general formula (G11),

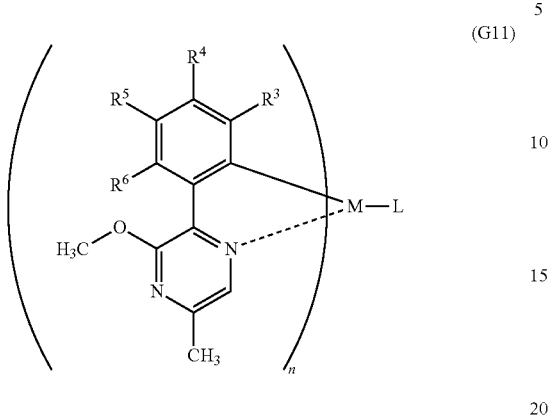
(G11)

wherein $R^3$ to $R^6$ individually represent hydrogen, an alkyl group, an alkoxy group, a halogen group, a haloalkyl group, an aryl group, a dialkylamino group, or a diarylamino group; M is a central metal and represents an element belonging to Group 9 or Group 10 in the periodic table; L represents a monoanionic ligand; and n is 2 when the M is an element belonging to Group 9, and n is 1 when the M is an element belonging to Group 10.

2. The organometallic complex according to claim 1, wherein the monoanionic ligand is any of structural formulae (L1) to (L8).

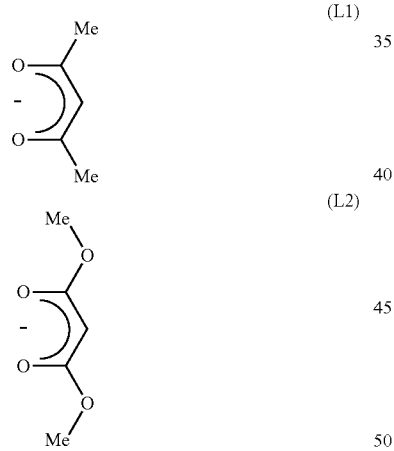

(L1)

(L2)

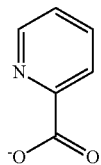
(L3)

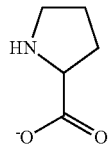
(L4)

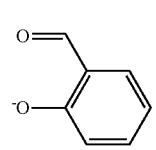
(L5)

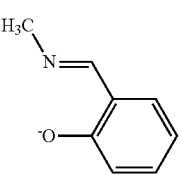
(L6)

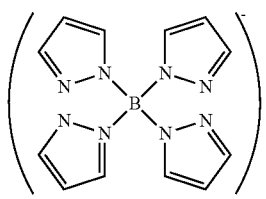
(L7)

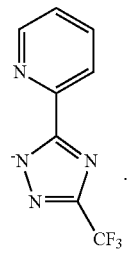
(L8)

3. The organometallic complex according to claim 1, wherein the M is iridium or platinum.

* * * * *